US010779762B2

(12) United States Patent
Yablonskiy et al.

(10) Patent No.: US 10,779,762 B2
(45) Date of Patent: Sep. 22, 2020

(54) MRI METHOD FOR IN VIVO DETECTION OF AMYLOID AND PATHOLOGY IN THE ALZHEIMER BRAIN

(71) Applicant: Washington University in St. Louis, St. Louis, MO (US)

(72) Inventors: Dmitriy Yablonskiy, Olivette, MO (US); Yue Zhao, St. Louis, MO (US)

(73) Assignee: Washington University, St. Louis, MO (US)

(*) Notice: Subject to any disclaimer, the term of this patent is extended or adjusted under 35 U.S.C. 154(b) by 190 days.

(21) Appl. No.: 15/770,127

(22) PCT Filed: Oct. 19, 2016

(86) PCT No.: PCT/US2016/057663
§ 371 (c)(1),
(2) Date: Apr. 20, 2018

(87) PCT Pub. No.: WO2017/070184
PCT Pub. Date: Apr. 27, 2017

(65) Prior Publication Data
US 2018/0310869 A1 Nov. 1, 2018

Related U.S. Application Data

(60) Provisional application No. 62/321,284, filed on Apr. 12, 2016, provisional application No. 62/243,940, filed on Oct. 20, 2015.

(51) Int. Cl.
*A61B 5/00* (2006.01)
*A61B 5/055* (2006.01)
(Continued)

(52) U.S. Cl.
CPC .......... *A61B 5/4088* (2013.01); *A61B 5/0042* (2013.01); *A61B 5/055* (2013.01); *A61B 5/14542* (2013.01); *G01R 33/50* (2013.01); *G01R 33/5601* (2013.01); *G01R 33/5608* (2013.01); *G01R 33/5616* (2013.01); *G01R 33/56366* (2013.01)

(58) Field of Classification Search
CPC ......... A61B 5/00; A61B 5/0033; A61B 5/004; A61B 5/0042; A61B 5/05; A61B 5/055; A61B 5/145; A61B 5/14542; A61B 5/40; A61B 5/4076; A61B 5/4088; G01R 33/00; G01R 33/20; G01R 33/44; G01R 33/48; G01R 33/50; G01R 33/54; G01R 33/56; G01R 33/5601; G01R 33/5608; G01R 33/561; G01R 33/5615; G01R 33/5616; G01R 33/563; G01R 33/56366
USPC ......................................... 324/300, 307, 309
See application file for complete search history.

(56) References Cited

U.S. PATENT DOCUMENTS

2004/0022736 A1    2/2004  Poduslo
2017/0198030 A1*   7/2017  Graham ................. C07K 16/18
(Continued)

OTHER PUBLICATIONS

Schuff et al., "MRI of hippocampal volume loss in early Alzheimer's disease in relation to ApoE genotype and biomarkers," Brain, 132:1067-1077, 2009.
(Continued)

*Primary Examiner* — Hoai-An D. Nguyen

(57) ABSTRACT

Disclosed are systems, biomarkers, and methods for the diagnosis of Alzheimer's Disease.

29 Claims, 8 Drawing Sheets

Figure 1:
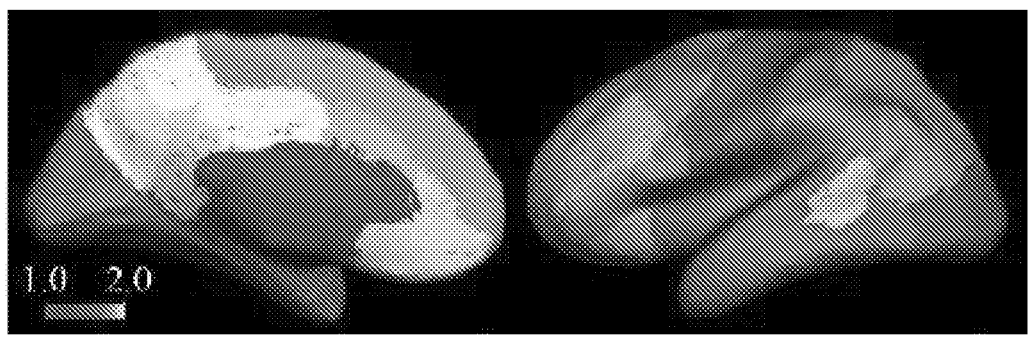

(51) Int. Cl.
*A61B 5/145* (2006.01)
*G01R 33/50* (2006.01)
*G01R 33/56* (2006.01)
*G01R 33/561* (2006.01)
*G01R 33/563* (2006.01)

(56) References Cited

U.S. PATENT DOCUMENTS

2018/0125853 A1* 5/2018 Lopez-Lopez ..... A61K 31/5377
2018/0203087 A1* 7/2018 Ye .................. G01R 33/56545

OTHER PUBLICATIONS

Selkoe, D. J., "Alzheimer's disease. In the beginning . . . ," Nature, 354(6353):432-433, 1991 (Abstract Only).
Spees et al., "Water proton MR properties of human blood at 1.5 Tesla: magnetic susceptibility, T(1), T(2), T*(2), and non-Lorentzian signal behavior," Magn Reson Med, 45(4):533-542, 2001 (Abstract Only).
Sperling et al., "Toward defining the preclinical stages of Alzheimer's disease: Recommendations from the National Institute on Aging-Alzheimer's Association workgroups on diagnostic guidelines for Alzheimer's disease," Alzheimers Dement, 7(3):280-292, 2011.
Su et al., "Quantitative Analysis of PiB-PET with FreeSurfer ROIs," PLos One, 8(11):e73377, 2013.
Thangavel et al., "Posterior parahippocampal gyrus pathology in Alzheimer's disease," Neuroscience, 154(2):667-676, 2008.
Ulrich et al., "Separation of Cellular and BOLD Contributions to T2* Signal Relaxation," Magn Reson Med, 75(2):606-615, 2016.
Wang et al., "Optimization Strategies for Evaluation of Brain Hemodynamic Parameters with qBOLD Technique," Magn Reson Med, 69(4):1034-1043, 2013.
Wen et al., "On the Role of Physiological Fluctuations in Quantitative Gradient Echo MRI—Implications for GEPCI, QSM and SWI," Magn Reson Med, 73(1):195-203, 2015.
Wen et al., "Detection and quantification of regional cortical gray matter damage in multiple sclerosis utilizing gradient echo MRI," NeuroImage: Clinical, 9:164-145, 2015.
Wengenack et al., "Regional differences in MRI detection of amyloid plaques in AD transgenic mouse brain," Neuroimage, 54(1):113-122, 2011.
Yablonskiy et al., "Quantitation of intrinsic magnetic susceptibility-related effects in a tissue matrix. Phantom study," Magn Reson Med, 39(3):417-428, 1998 (Abstract Only).
Yablonskiy et al., "Theory of NMR signal behavior in magnetically inhomogeneous tissues: the static dephasing regime," Magn Reson Med, 32(6):749-763, 1994 (Abstract Only).
Yablonskiy et al., "Voxel Spread Function (VSF) Method for Correction of Magnetic Field Inhomogeneity Effects in Quantitative Gradient-Echo-Based MRI," Magn Reson Med, 70(5):1283-1292, 2013.
Yablonskiy et al., "BOLD-based Techniques for Quantifying Brain Hemodynamic and Metabolic Properties—Theoretical Models and Experimental Approaches," NMR Biomed, 26(8):963-986, 2013.
Yablonskiy et al., "Biophysical mechanisms of MRI signal frequency contrast in multiple sclerosis," Proc Natl Acad Sci, 109(35):14212-14217, 2012.
Zhao et al., "On the Relationship between Cellular and Hemodynamic Properties of the Human Brain Cortex throughout Adult Lifespan," Neuroimage, 133:417-429, 2016 (Abstract Only).
Albert et al., "The diagnosis of mild cognitive impairment due to Alzheimer's disease: Recommendations from the National Institute on Aging-Alzheimer's Association workgroups on diagnostic guidelines for Alzheimer's disease," Alzheimers Dement, 7(3):270-279, 2011.

Arnold et al., "The topographical and neuroanatomical distribution of neurofibrillary tangles and neuritic plaques in the cerebral cortex of patients with Alzheimer's disease," Cereb Cortex, 1(1):103-116, 1991 (Abstract Only).
Bateman et al., "Clinical and Biomarker Changes in Dominantly Inherited Alzheimer's Disease," N Engl J Med, 367:795-804, 2012.
Benveniste et al., "Detection of neuritic plaques in Alzheimer's disease by magnetic resonance microscopy," Proc Natl Acad Sci, 96(24):14079-14084.
Benzinger et al., "Regional variability of imaging biomarkers in autosomal dominant Alzheimer's disease," Proc Natl Acad Sci USA, 110(47):E4502-4509, 2013.
Braak et al., "Neuropathological stageing of Alzheimer-related changes," Acta Neuropathol, 82(4):239-259, 1991 (Abstract Only).
Braak et al., "Staging of Alzheimer's disease-related neurofibrillary changes," Neurobiol Aging, 16(3):271-278, 1995 (Abstract Only).
Braak et al., "Frequency of stages of Alzheimer-related lesions in different age categories," Neurobiol Aging, 18(4):351-357, 1997 (Abstract Only).
Braak et al., "Stages of the pathologic process in Alzheimer disease: age categories from 1 to 100 years," J Neuropathol Exp Neurol, 70(11):960-969, 2011 (Abstract Only).
Chamberlain et al., "Comparison of amyloid plaque contrast generated by T2-, T2*-, and susceptibility-weighted imaging methods in transgenic mouse models of Alzheimer's disease," Magn Reson Med, 61(5):1158-1164, 2009.
Dickerson et al., "Alzheimer-signature MRI biomarker predicts AD dementia in cognitively normal adults," Neurology, 76(16):1395-1402, 2011.
Dickson et al., "Quantitative phenomenological model of the BOLD contrast mechanism," J Magn Reson, 212(1):17-25, 2011 (Abstract Only).
Fagan et al., "The search for antecedent biomarkers of Alzheimer's disease," J Alzheimers Dis, 8(4):347-358, 2005 (Abstract Only).
Fagan et al., "Longitudinal change in CSF biomarkers in autosomal-dominant Alzheimer disease," Sci Transl Med, 6(226): 226ra30, 2014.
Gomez-Isla et al., "Profound Loss of Layer II Entorhinal Cortex Neurons Occurs in Very Mild Alzheimer's Disease," J Neurosci, 16(14):4491-4500.
Hardy et al., "Alzheimer's disease: the amyloid cascade hypothesis," Science, 256(5054):184-185, 1992 (Abstract Only).
Hardy et al., "The amyloid hypothesis of Alzheimer's disease: progress and problems on the road to therapeutics," 297 (5590):356-356, 2002 (Abstract Only).
Hardy et al., "Amyloid deposition as the central event in the aetiology of Alzheimer's disease," Trends Pharmacol Sci, 12(10):383-388, 1991 (Abstract Only).
He et al., "Quantitative BOLD: Mapping of Human Cerebral Deoxygenated Blood Volume and Oxygen Extraction Fraction: Default State," Magn Reson Med, 57(1):115-126, 2007.
He et al., "Validation of Oxygen Extraction Fraction Measurement by qBOLD Technique," Magn Reson Med, 60(4):882-888, 2008.
Oxford University Press, Hoesen GWV, "The human parahippocampal region in Alzheimer's disease, dementia, and ageing" The parahippocampal region: organization and role in cognitive function, Oxford, New York, Section 4, p. 271-290, 2002 (Abstract Only).
Hyman et al., "Alzheimer's disease: cell-specific pathology isolates the hippocampal formation," Science, 225(4667):1168-1170, 1984 (Abstract Only).
Ikonomovic et al., "Post-mortem correlates of in vivo PiB-PETamyloid imaging in a typical case of Alzheimer's disease," Brain, 131:1630-1645, 2008.
Jack et al., "Hypothetical model of dynamic biomarkers of the Alzheimer's pathological cascade," Lancet Neurol, 9(1):119, 2010.
Jack et al., "Rates of Hippocampal Atrophy Correlate with Change in Clinical Status in Aging and AD," 55(4):484-489, 2000.
Jenkinson et al., "Improved optimization for the robust and accurate linear registration and motion correction of brain images," Neuroimage, 17(2):825-841, 2002 (Abstract Only).
Jenkinson et al., "FSL," Neuroimage, 62(2): 782-790, 2012 (Abstract Only).

(56) References Cited

OTHER PUBLICATIONS

Juottonen et al., "Major decrease in the volume of the entorhinal cortex in patients with Alzheimer's disease carrying the apolipoprotein E epsilon 4 allele," J Neurol Neurosurg Psychiatry, 65:322-327, 1998.

Klunk et al., "Imaging Brain Amyloid in Alzheimer's Disease with Pittsburgh Compound-B," Ann Neurol, 55:306-319, 2004.

Lee et al., "Visualization of β-Amyloid Plaques in a Transgenic Mouse Model of Alzheimer's Disease Using MR Microscopy Without Contrast Reagents," Magn Reson Med, 52(3):538-544, 2004.

Luo et al., "Gradient echo MRI correlates with clinical measures and allows visualization of veins within MS lesions," Mult Scler, 20(3):349-355, 2014.

Luo et al., "Gradient Echo Plural Contrast Imaging—signal model and derived contrasts: T*2, T1, Phase, SWI, T1f, FST2* and T2*-SWI," Neuroimage, 60(2):1073-1082, 2012.

Maeda et al., "In vivo positron emission tomographic imaging of glial responses to amyloid-β and tau pathologies in mouse models of Alzheimer's disease and related disorders," J Neurosci, 31(12):4720-4730, 2011.

Mamah et al., "Subcomponents of brain T2* relaxation in schizophrenia, bipolar disorder and siblings: A Gradient Echo Plural Contrast Imaging (GEPCI) study," Schizophr Res, 169(0):36-45, 2015.

McKhann et al., "The diagnosis of dementia due to Alzheimer's disease: Recommendations from the National Institute on Aging-Alzheimer's Association workgroups on diagnostic guidelines for Alzheimer's disease," Alzheimers Dement, 7(3):263-269, 2011.

Meadowcroft et al., "Magnetic Resonance Imaging and Histological Analysis of Beta-Amyloid Plaques in Both Human Alzheimer's Disease and APP/PS1 Transgenic Mice," J Magn Reson Imaging, 29(5):997-1007, 2009.

Mintun et al., "[11C]PIB in a nondemented population: potential antecedent marker of Alzheimer disease," Neurology, 67(3):446-452, 2006 (Abstract Only).

Mitchell et al., "Parahippocampal Tau Pathology in Healthy Aging, Mild Cognitive Impairment, and Early Alzheimer's Disease," Ann Neurol, 51:182-189, 2002.

Morris, J.C., "The Clinical Dementia Rating (CDR): current version and scoring rules," Neurology, 43(11):2412-2414, 1993 (Abstract Only).

Morris et al., "Developing an international network for Alzheimer research: The Dominantly Inherited Alzheimer Network," Clin Investig (Lond), 2(10):975-984, 2012.

Mugler et al., "Threedimensional magnetization prepared rapid gradient-echo imaging (3D MP RAGE)," Magn Reson Med, 15(1):152-157, 1990 (Abstract Only).

Ogawa et al., "Brain magnetic resonance imaging with contrast dependent on blood oxygenation," Proc Natl Acad Sci USA, 87"9868-9872, 1990.

Patel et al., "Detection of cortical lesions in multiple sclerosis: A new imaging approach," MSJ: Exptl Translational Clinical, 1:1-4, 2015.

Price et al., "Tangles and Plaques in Nondemented Aging and "Preclinical" Alzheimer's Disease," Ann Neurol, 45:358-368, 1999.

Price et al., "Kinetic modeling of amyloid binding in humans using PET imaging and Pittsburgh Compound-B," J Cereb Blood Flow Metab, 25(11):1528-1547, 2005 (Abstract Only).

Price et al., "Kinetic modeling of amyloid binding in humans using PET imaging and Pittsburgh Compound-B," Arch Neurol, 58(9):1395-1402, 2001.

Quirk et al., "Optimal Decay Rate Constant Estimates from Phased Array Data Utilizing Joint Bayesian Analysis," J Magn Reson, 198(1):49-56, 2009.

Reuter et al., "Within-subject template estimation for unbiased longitudinal image analysis," Neuroimage, 61(4):1402-1418, 2012.

Sati et al., "In vivo Quantitative evaluation of brain tissue damage in Multiple Sclerosis using Gradient Echo Plural Contrast Imaging technique," Neuroimage, 51(3):1089-1097, 2010.

Scharfman et al., Preface, Annals of the New York Acad Sci, 911(1):ix-xiii, 2000 (Abstract Only).

* cited by examiner

MRI METHOD FOR IN VIVO DETECTION OF AMYLOID AND PATHOLOGY IN THE ALZHEIMER BRAIN

This application claims the benefit of U.S. Provisional Application No. 62/243,940, filed on Oct. 20, 2015 and U.S. Provisional Application No. 62/321,284, filed on Apr. 12, 2016, which are incorporated herein by reference in their entirety.

This invention was made with government support under UL1 TR000448 awarded by NIH National Center for Advancing Translational Sciences and grants P50AG05681 and P01AG03991 awarded by the National Institutes of Health. The government has certain rights in the invention.

I. BACKGROUND

Alzheimer's Disease (AD) is a chronic neurodegenerative disease affecting between 21 and 35 million people worldwide. It most often begins in people over 65 years of age, although 4% to 5% of cases are early-onset Alzheimer's which begin before this. It affects about 6% of people 65 years and older. As the disease advances, symptoms can include problems with language, disorientation (including easily getting lost), mood swings, loss of motivation, not managing self care, and behavioral issues. As a person's condition declines, they often withdraw from family and society. Gradually, bodily functions are lost, ultimately leading to death. Although the speed of progression can vary, the average life expectancy following diagnosis is three to nine years. Currently, there are no treatments stop or reverse its progression, though some may temporarily improve symptoms.

Alzheimer's disease is usually diagnosed based on the person's medical history, history from relatives, and behavioral observations. Current research efforts are focused on detecting AD in its preclinical phase before there is significant and irreversible neuronal loss. The presence of characteristic neurological and neuropsychological features and the absence of alternative conditions is supportive. Advanced medical imaging with computed tomography (CT), and with single-photon emission computed tomography (SPECT) or positron emission tomography (PET) can be used to help exclude other cerebral pathology or subtypes of dementia. Moreover, it may predict conversion from prodromal stages (mild cognitive impairment) to Alzheimer's disease. Importantly, newer PET compounds allow direct detection of amyloid plaques. However, PET exam relies on expensive machinery and procedures that are not available in many hospitals and PET is associated with concerns of radiation exposure. What is needed are novel broadly available non-invasive approaches for assessing brain tissue pathology in AD that can be used for screening population especially for early, preclinical changes in AD brain.

II. SUMMARY

Disclosed are methods and systems related to the detection and diagnosis of Alzheimer's Disease.

In one aspect, disclosed herein are methods of measuring β-amyloid in a subject comprising obtaining a scan of the brain of a subject using gradient echo magnetic resonance imaging (MRI) technique (such as, for example, gradient echo plural contrast imaging (GEPCI)), measuring tissue specific R2* values in specific brain regions (including, but not limited to precuneus, fusiform, lingual, paracentral, rostral-anterior cingulate, and parahippocampus); wherein an increase in tissue specific R2* relative to a normal control ($\Delta R2^*$) indicates that the subject has increased accumulation of β-amyloid.

Also disclosed are methods of measuring β-amyloid of any preceding aspect, further comprising using a voxel spread function method to account for the adverse effects of the background field inhomogeneities to accurately measure tissue specific R2*.

Also disclosed are methods of measuring β-amyloid of any preceding aspect, further comprising using navigator echoes to account for the adverse effects of physiological fluctuations to accurately measure tissue specific R2*.

Also disclosed are methods of measuring β-amyloid of any preceding aspect, further comprising accounting for oxygen extraction fraction, deoxygenated cerebral blood volume, and the concentration of tissue deoxyhemoglobin to separate cellular and vascular contributions to tissue specific R2* measurements.

In one aspect, disclosed herein are methods of measuring loss of cellular integrity in the brain of a subject comprising obtaining a scan of the brain of a subject using gradient echo magnetic resonance imaging (MRI) technique (such as, for example gradient echo plural contrast imaging (GEPCI)), measuring tissue specific R2t* values in specific brain regions (including, but not limited to hippocampus); wherein a decrease in tissue specific R2t* relative to a normal control ($\Delta R2t^*$) indicates that the subject has decreased cellular integrity in the brain beyond simply atrophy.

In one aspect, the loss of cellular density/integrity is directly indicative of AD. Accordingly, in one aspect, disclosed herein are method of diagnosing AD in a subject comprising obtaining a scan of the brain of a subject using gradient echo magnetic resonance imaging (MRI) technique (such as, for example, gradient echo plural contrast imaging (GEPCI)), measuring tissue specific R2t* values in specific brain regions (including hippocampus); wherein a decrease in tissue specific R2t* relative to a normal control (decreased $\Delta R2t^*$) indicates that the subject has decreased cellular integrity consistent with a diagnosis of AD (i.e., the subject has AD).

In one aspect, disclosed herein are methods of diagnosing the progression of AD in a subject comprising obtaining a scan of the brain of a subject using gradient echo magnetic resonance imaging (MRI) technique (such as, for example gradient echo plural contrast imaging (GEPCI)), measuring tissue specific R2* values in specific brain regions (including, but not limited to precuneus, fusiform, lingual, paracentral, rostral-anterior cingulate, and parahippocampus); measuring tissue specific R2t* values in specific brain regions (including, but not limited to hippocampus); wherein R2* and R2t* are each unchanged relative to a normal control ($\Delta R2^*$ and $\Delta R2t^*$ are each 0) which indicates that the subject does not have AD; wherein and increase in R2* and a normal R2t* relative to a normal control (increased $\Delta R2^*$ and unchanged R2t* (i.e., $\Delta R2t^*$ is 0)) indicates that the subject has pre-clinical AD; and wherein an increase in R2* and a decrease in R2t* relative to a normal control increased $\Delta R2^*$ and decreased $\Delta R2t^*$) indicates that the subject has clinical AD (for example mild AD).

Also disclosed are methods of diagnosing AD of any preceding aspect, further comprising measuring accumulation of tau proteins in the brain.

In another aspect, disclosed herein are biomarkers for AD, wherein the biomarker is the $\Delta R2^*$ obtained from gradient echo MRI (e.g., GEPCI) measured in the precuneus, fusiform, lingual, paracentral, rostral-anterior cingulate, and/or parahippocampus region of the brain.

Also disclosed herein are biomarkers for AD, wherein the biomarker is a surrogate measurement of tissue cellular density/integrity, $\Delta R2t^*$, obtained from gradient echo MRI (e.g., GEPCI) measured in the hippocampus of the brain.

In another aspect, disclosed herein is a system for measuring amyloid concentration in the brain comprising an MRI device, a processor for determining the $\Delta R2^*$ and the phenomenological relationship between $\Delta R2^*$ and $\beta$-amyloid concentration, and a display.

Also disclosed are systems of any preceding aspect, wherein the processor further accounts for the contribution of magnetic field inhomogeneities and artifacts related to physiological fluctuations on transverse relaxation, as well as calculating oxygen extraction fraction, deoxygenated cerebral blood volume, and/or the concentration of tissue deoxyhemoglobin.

Also disclosed are systems of any preceding aspect, further comprising a processor for determining the $\Delta R2t^*$ in specific regions of the brain and the phenomenological relationship between $\Delta R2t^*$ and loss of tissue cellular density/integrity.

Also disclosed are systems of any preceding aspect, wherein the processor for determining the $\Delta R2t^*$ and the $\Delta R2^*$ is the same processor.

In one aspect, disclosed herein are systems for measuring loss of tissue cellular density/integrity in the brain comprising an MRI device; a processor for determining the R2t* in specific regions of the brain and the phenomenological relationship between R2t* and loss of tissue cellular density/integrity, and a display.

Also disclosed are systems for diagnosing Alzheimer's disease comprising an MRI device, a processor for determining the $\Delta R2^*$ and $\Delta R2t^*$ in regions of the brain, a phenomenological relationship between $\Delta R2^*$ and $\Delta R2t^*$ in regions of the brain and severity of Alzheimer's disease, and a display.

Also disclosed are systems for diagnosing Alzheimer's disease comprising an MRI device; a processor for determining a combination of GEPCI surrogate markers of $\beta$-amyloid burden, $\Delta R2^*$, and tissue cellular loss/integrity, $\Delta R2t^*$; a processor for distinguishing between normal, preclinical, and mild AD groups; and a display.

Also disclosed are systems for diagnosing Alzheimer's disease of any preceding aspect, wherein the processor for determining the combination of GEPCI surrogate markers and the processor for distinguishing between normal, preclinical, and mild AD groups is the same processor.

III. BRIEF DESCRIPTION OF THE DRAWINGS

The accompanying drawings, which are incorporated in and constitute a part of this specification, illustrate several embodiments and together with the description illustrate the disclosed compositions and methods.

FIG. 1 shows an example of the map of GEPCI-estimated $_{amyloid}$SUVR.

Figure 2:
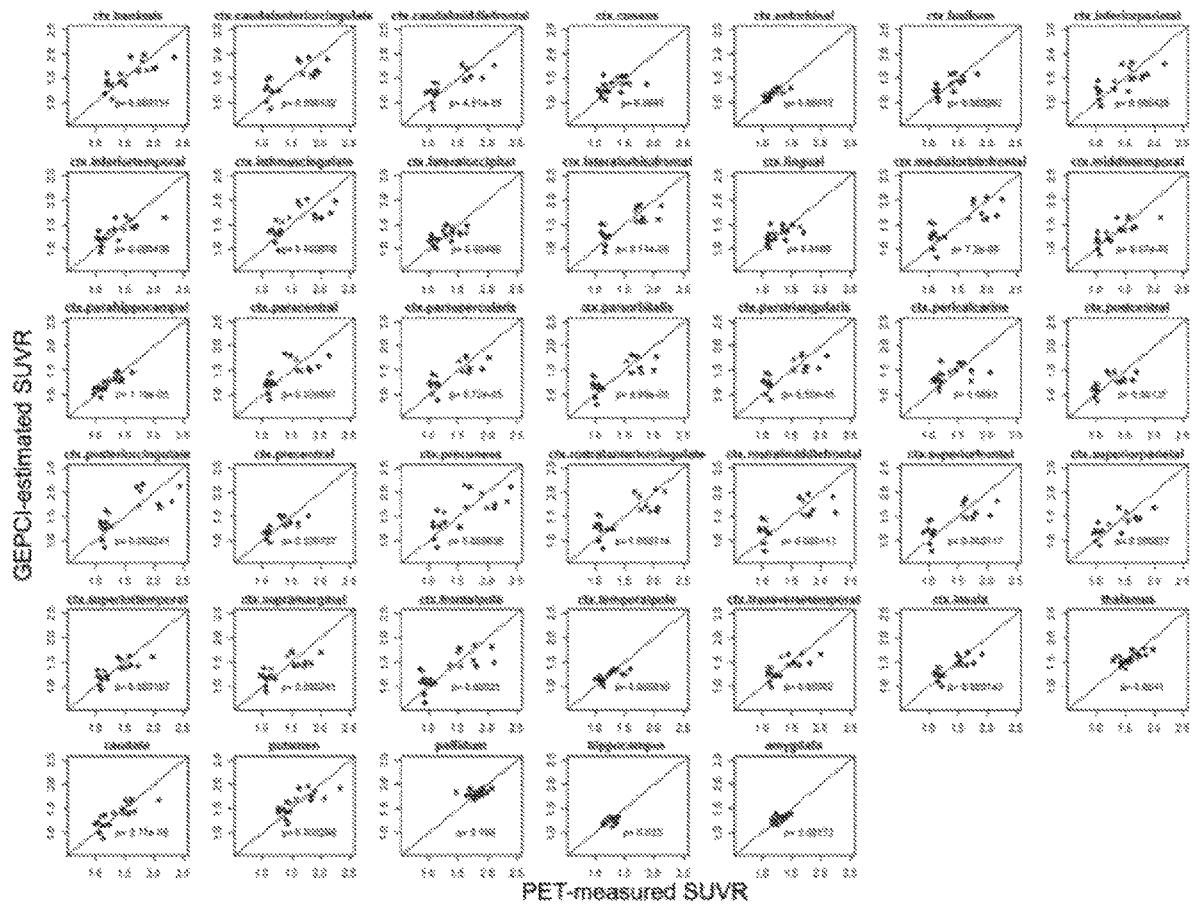

FIG. 2. GEPCI-estimated vs. PET-measured amyloid SUVR in all subjects for different brain regions. Results are based on measuring R2* in parahippocampal region of the brain. It doesn't work for cortex cerebellum because it is used as a reference for calculating PET SUVR and it is 1.0 in all subjects.

Figure 3:
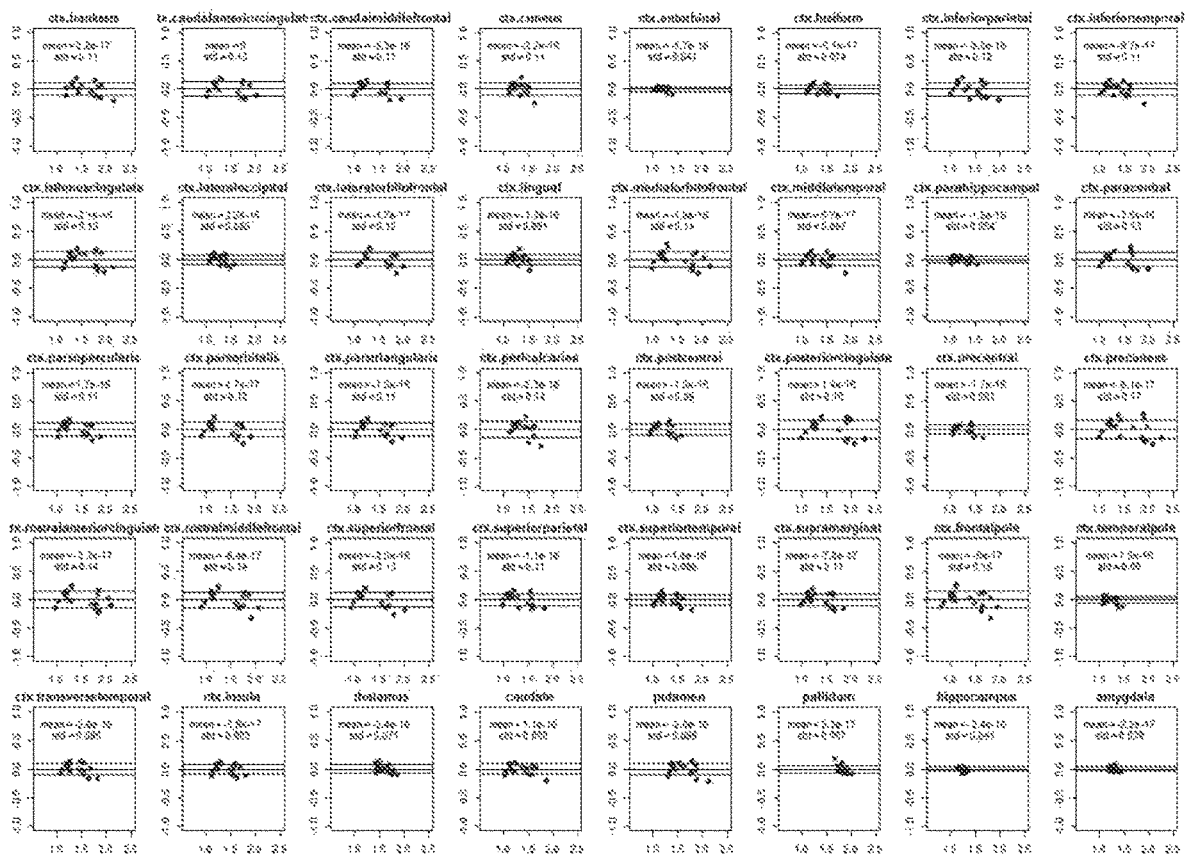
Figure 4:
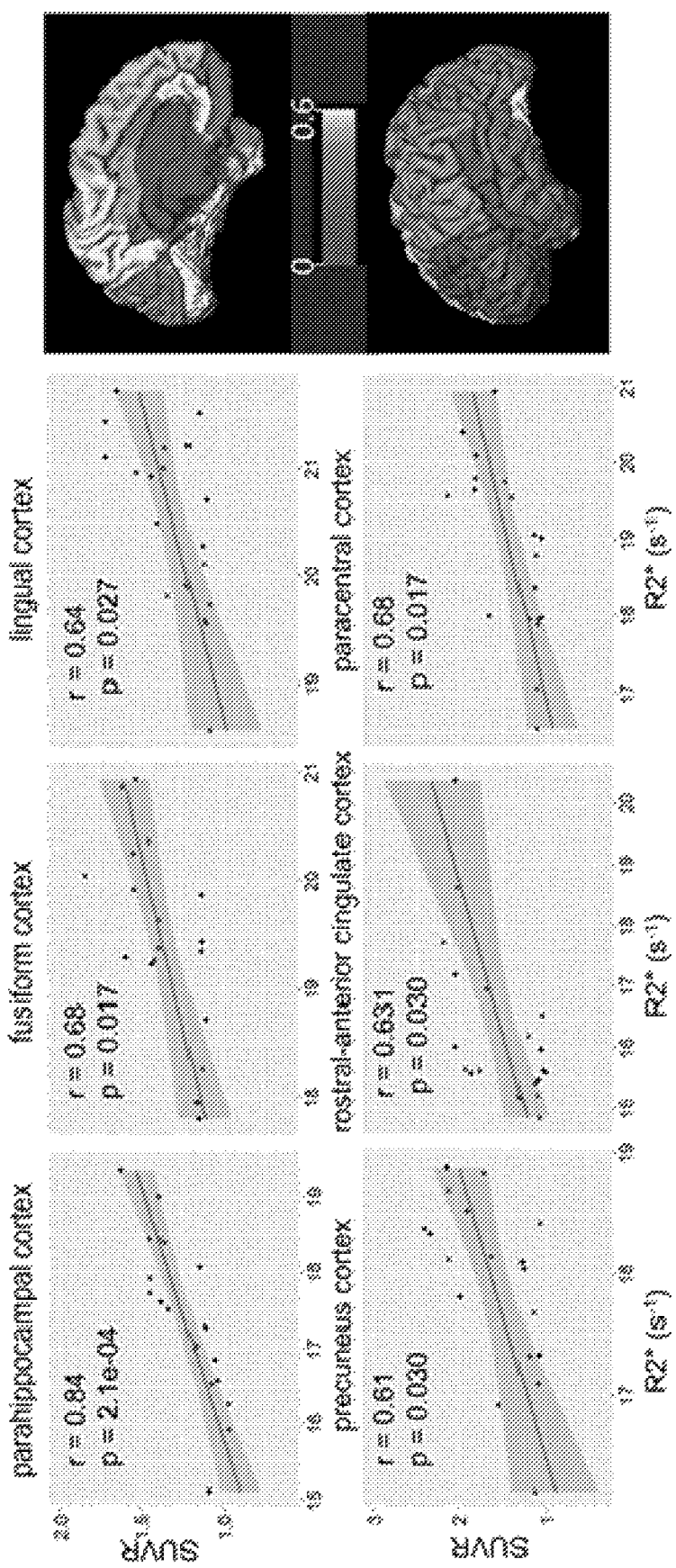

FIG. 3 shows Bland-Altman plots comparing GEPCI-estimated vs. PET-measured amyloid SUVR in all subjects for different brain regions. Each point represents a single subject. Blue points—subjects with CDR 0, red points—subjects with positive CDR (0.5 or 1). Horizontal lines show mean value of the difference between PET-measured SUVR and GEPCI-estimated SUVR and ±1.96 STD of these differences. Data show a very high correlation with mean differences essentially zero and standard deviations of about 0.1 in SUVR units FIG. 4 shows the correlation between PET PiB A$\beta$ SUVR (dimensionless) and R2* (s-1) relaxation rate constant obtained in 19 participants. Plots show examples of correlation in several brain regions. Each point represents a single participant. Shaded areas represent 95% confidence intervals of the linear fits (solid lines). Pearson correlation coefficients (r) and p values (corrected for multiple comparison using false discovery rate over all cortical regions) are shown in the left upper corners. The surface maps on the right represent r values in all cortical areas. The image segmentation is based on the FreeSurfer software. The data show significant correlations not only in the areas of high A$\beta$ accumulation (e.g. precuneus) but also in the areas of MTL, such as the parahippocampal cortex and the fusiform cortex. Remarkably, the strongest and most significant correlation exists in the parahippocampal cortex—the area of low A$\beta$ accumulation.

Figure 5:
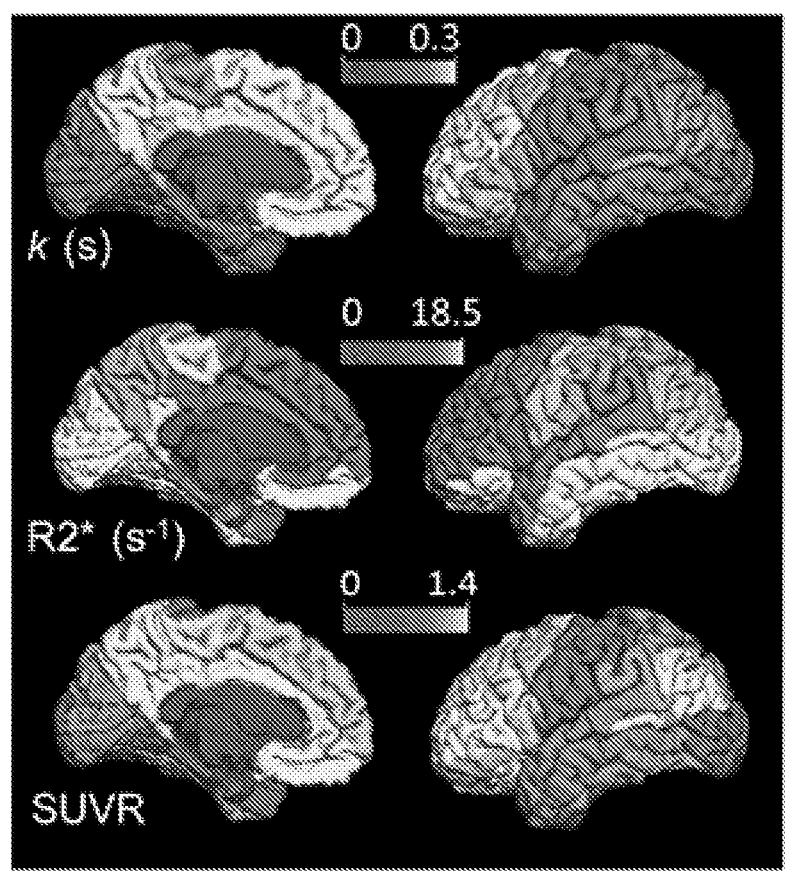

FIG. 5 shows the upper row represents the surface maps of the slopes (units of sec) of linear regression (coefficient k in Eq. [8] and [9]) between regional PET-measured A$\beta$ SUVR and parahippocampal R2* across 19 participants. All regional slopes are positive. The coefficients of the linear regressions are listed in Table 1. The second and the last rows represent the averaged cortical mean values of R2* and A$\beta$ SUVR across the same 19 participants. White matter, deep gray matter and ventricles were excluded. The image segmentation is based on the FreeSurfer software.

Figure 6:
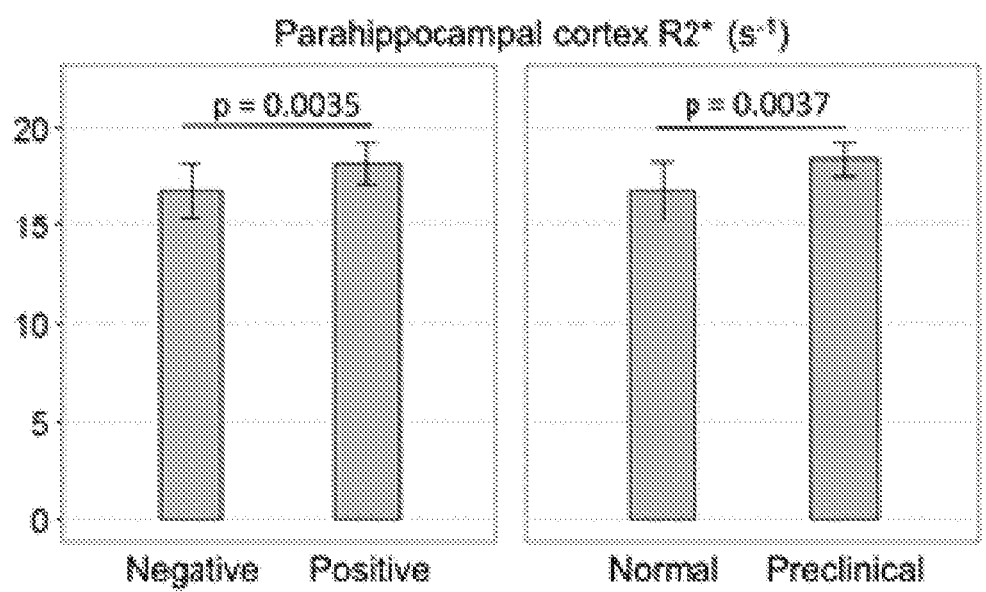

FIG. 6 shows a group comparison based on the R2* measurements in the parahippocampal cortex. The bar graph on the left shows significant differences between all participants (independent of CDR) with negative (n=15, R2*=16.79±1.40 s-1) and positive (n=19, R2*=18.20±1.08 s-1) A$\beta$ status (see definition in the Methods). The bar graph on the right shows significant differences between normal group (CDR=0, A$\beta$ negative, n=13, R2*=16.77±1.51 s-1) and preclinical group (CDR=0, A$\beta$ positive, n=10, R2*=18.41±0.84 s-1).

Figure 7:
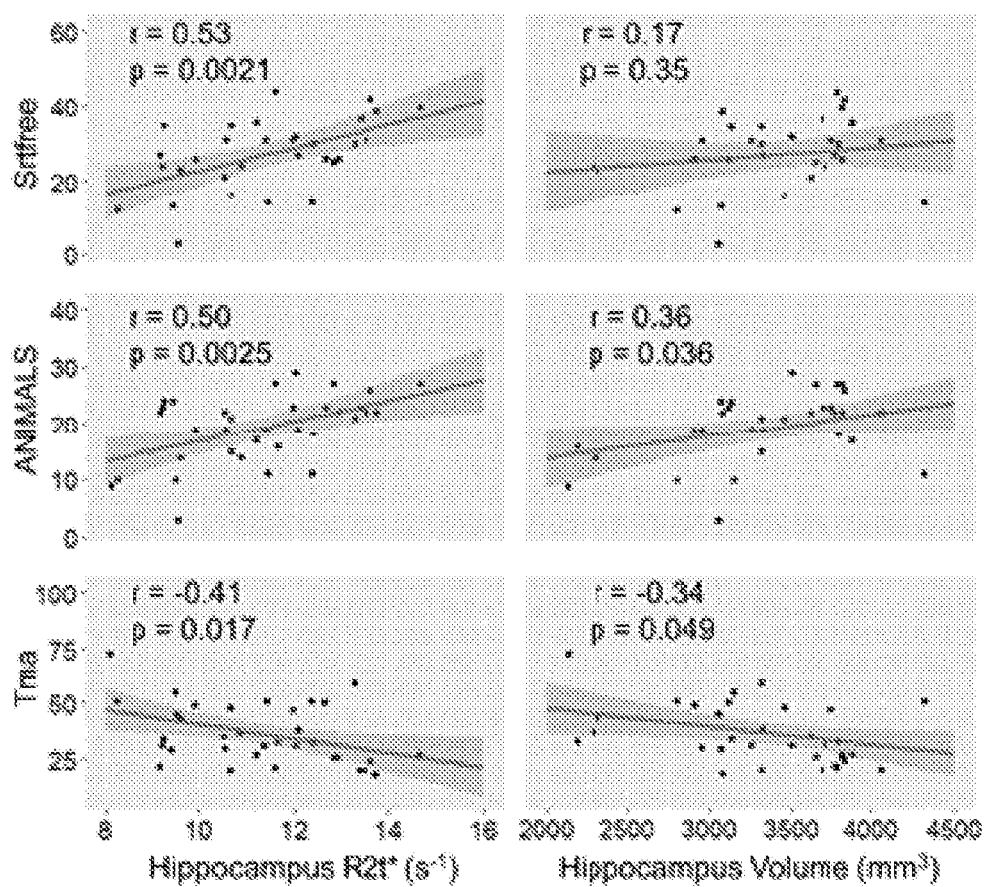

FIG. 7 shows the correlation between cognitive tests performance and hippocampal R2t*. Cognitive measures included Free and Cued Selective Reminding Test (Srtfree), Animal Naming (ANIMALS), and Trail making Test Part A completion time (Tma). Note that higher scores on Tma indicate worse performance. Correlations with hippocampal volume are also presented for comparison. Each point represents a single participant (n=34). Shaded areas represent 95% confidence intervals of linear fits (solid lines). Pearson correlation coefficients (r) and p values are shown in the left upper corners.

Figure 8:
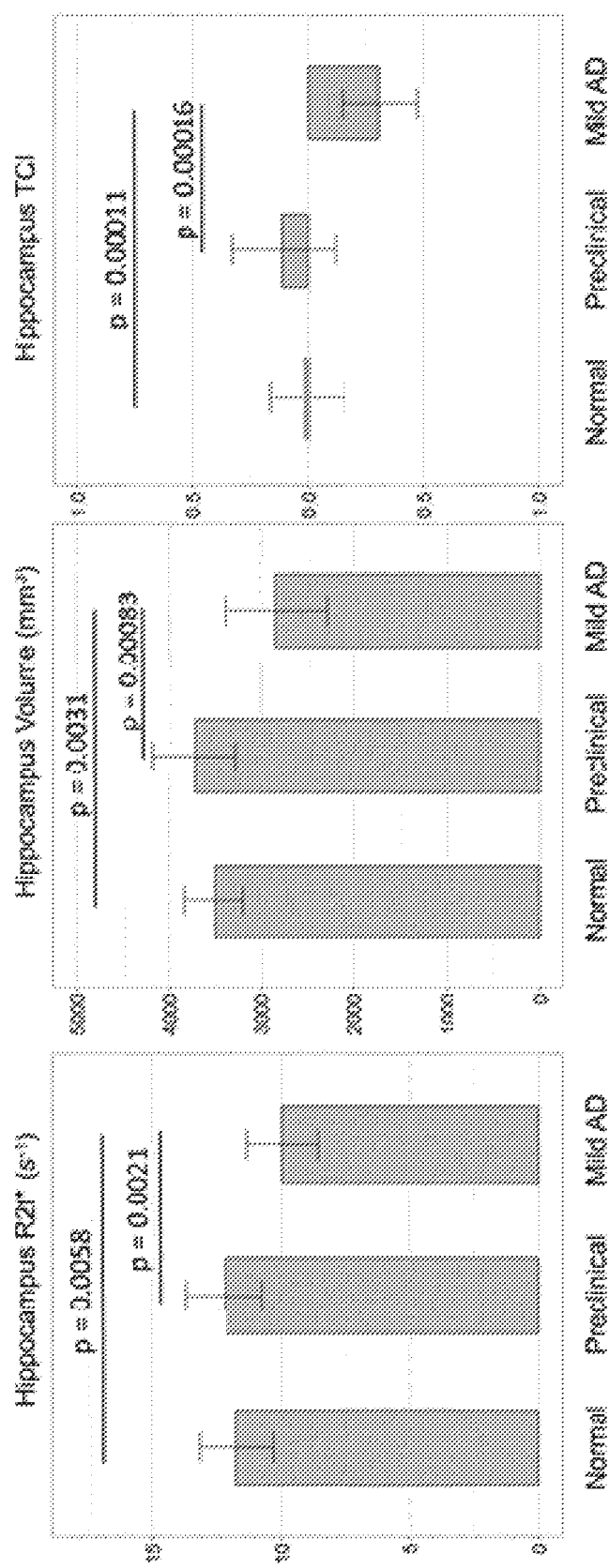

FIG. 8 shows bar graphs show the data obtained in the hippocampus of 34 participants. Bars represent mean values and error bars are standard deviations. Data are separated into three groups: Normal, preclinical AD and mild AD (CDR 0.5 or 11 GEPCI R2t* and volumes are shown. Also shown is the parameter TCI (tissue content index, Eq.[5]). While R2t* can serve as a surrogate marker of neuronal density/integrity, the TCI can serve as a surrogate marker characterizing a change in the total neuronal content. The results are summarized in Table 2.

IV. DETAILED DESCRIPTION

Before the present devices, and/or methods are disclosed and described, it is to be understood that they are not limited to specific MRI scanners unless otherwise specified, or to particular methods of data analysis unless otherwise specified, as such may, of course, vary. It is also to be understood that the terminology used herein is for the purpose of describing particular embodiments only and is not intended to be limiting.

A. DEFINITIONS

As used in the specification and the appended claims, the singular forms "a," "an" and "the" include plural referents unless the context clearly dictates otherwise. Thus, for example, reference to "a MRI scanner or biomarker" includes mixtures multiple scanners and biomarkers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15 It is also understood that each unit between two particular units are also disclosed. For example, if 10 and 15 are disclosed, then 11, 12, 13, and 14 are also disclosed.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

As used herein, "equivalent" means statistically unchanged or identical values between to measures. Where $\Delta R2^*$ and $\Delta R2t^*$ refer to a comparison of $R2^*$ and $R2t^*$ values in a subject relative to a normal control, an equivalent $R2^*$ and/or $R2t^*$ would result in $\Delta R2^*$ of approximately 0 and a $\Delta R2t^*$ of approximately 0 (i.e., statistically no change).

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

Alzheimer's disease is characterized by loss of neurons and synapses in the cerebral cortex and certain subcortical regions. This loss results in gross atrophy of the affected regions, including degeneration in the temporal lobe and parietal lobe, and parts of the frontal cortex and cingulate gyms. Degeneration is also present in brainstem nuclei like the locus coeruleus. Studies using MRI and PET have documented reductions in the size of specific brain regions in people with AD as they progressed from mild cognitive impairment to Alzheimer's disease, and in comparison with similar images from healthy older adults.

Both amyloid plaques and neurofibrillary tangles are clearly visible by microscopy in brains of those afflicted by AD. Plaques are dense, mostly insoluble deposits of beta-amyloid peptide and cellular material outside and around neurons. Tangles (neurofibrillary tangles) are aggregates of the microtubule-associated protein tau which has become hyperphosphorylated and accumulate inside the cells themselves. Although many older individuals develop some plaques and tangles as a consequence of ageing, the brains of people with AD have a greater number of them in specific brain regions such as the temporal lobe. Lewy bodies are not rare in the brains of people with AD.

Many studies have shown that cerebral atrophy is significantly greater in patients with Alzheimer disease (Alzheimer's disease) than in persons without it. However, the variability of atrophy in the normal aging process makes it difficult to use MRI-measured atrophy as a definitive diagnostic technique. Nevertheless, the volume loss can be characteristic for many other neurological diseases. More direct in vivo measure of AD is evaluation of amyloid accumulation was only available with PET and not available with MRI prior to the present disclosure. Thus, until the present disclosure, the evaluation of amyloid accumulation and loss of tissue cellular density and integrity was not possible with MRI (and CT for that matter).

Disclosed herein is the use of MRI to detect changes in the brain tissue of subjects with Alzheimer Disease (AD) related to accumulation of amyloid and loss of tissue cellular density and integrity in an AD brain tissue. The major supposition is that accumulation of amyloid in the brain leads to changes in MRI signal relaxation properties of AD brain tissue, such as, for example, changes tissue specific $R2^*$ values and these changes should be correlated with the amount of accumulated amyloid. Additionally some underlying pathological changes in the AD brain can also cause changes in the tissue specific $R2^*$ values and also lead to accumulation of amyloid, and these two measures (changes in $R2^*$ and concentration of amyloid) can be correlated. Specifically, by calculating difference, $\Delta R2^*$, between $R2^*$ values in a given subject and age-matched normal $R2^*$ estimated from a baseline of control subjects, a measure of β-amyloid accumulation can be made. Accordingly, and in one aspect, disclosed herein are methods of measuring β-amyloid in a subject comprising obtaining a scan of the brain of a subject using gradient echo magnetic resonance imaging (MRI) technique, measuring tissue specific $R2^*$ values in specific brain regions (including, but not limited to precuneus, fusiform, lingual, paracentral, rostral-anterior cingulate, and parahippocampus)); wherein an increase in tissue specific $R2^*$ relative to a normal control (i.e., an increased $\Delta R2^*$) indicates that the subject has increased accumulation of β-amyloid. Because an increase in $\Delta R2^*$ correlates directly with β-amyloid accumulation, it is clear that $\Delta R2^*$ is a new biomarker for β-amyloid accumulation and AD. Accordingly, and in one aspect, disclosed herein is a biomarker for AD, wherein the biomarker is the $\Delta R2^*$ obtained from gradient echo MRI (e.g., GEPCI) measured in the any region of the brain (including, but not limited to, for example, the precuneus, the parahippocampal region of the brain, fusiform, entorhinal, paracentral, lingual, superiorfrontal, transversetemporal, precentral, postcentral).

Herein a novel advanced approach that was developed allows to separate the total $R2^*$ relaxation into tissue-specific ($R2t^*$) and contributions from magnetic susceptibility inclusions. The non-linear function $f_s$ describes the signal decay due to the presence of magnetic susceptibility inclusions. This approach can account for different types of inclusions, e.g. blood vessel network (BOLD effect), trabecular bone, iron oxide nanoparticles, etc. and was used herein for modeling transverse relaxation of GRE signal created by amyloid plaques that are known to create $R2^*$ signal decay. Since no correlation exists between amyloid accumulation and BOLD effect, the correlation between amyloid accumulation and $R2^*$, that was found in AD patients (see below), was mostly related to magnetic susceptibility effects created by amyloid plaques. Since $R2t^*$ describes the part of the signal decay resulting from water molecules interaction with cellular components of biological tissues, it is sensitive to cellular alterations in human brain. Gradient echo MRI (e.g., GEPCI)-derived tissue specific structural and functional metrics show that the parameter $R2t^*$ is related to the neuronal tissue density. Specifically, by calculating difference, $\Delta R2t^*$, between $R2t^*$ values in a given subject and age-matched normal $R2t^*$ estimated from a baseline of control subjects, a measure of neuronal cellular integrity/density can be made. Where $R2t^*$ is related to neuronal density/integrity, the product of $R2t^*$ and the hippocampal volume (V) can characterize the total neuronal content in the hippocampus. To characterize the global tissue change in the hippocampus, it is convenient to introduce the Tissue Content Index (TCI) which is a biomarker for total neuronal content loss. Accordingly, disclosed herein are methods of measuring loss of cellular integrity/density in the brain of a subject comprising obtaining a scan of the brain of a subject using gradient echo magnetic resonance imaging (MRI) technique, measuring tissue specific $R2t^*$ values in specific brain regions (including hippocampus); wherein a decrease of $R2t^*$ in some specific brain regions relative to a normal control (i.e., decreased $\Delta R2t^*$) corresponds to the loss of tissue cellular integrity. Moreover, because a decrease in $\Delta R2t^*$ directly correlates with loss of cellular integrity/density in the brain (e.g., the hippocampus), $\Delta R2t^*$ is a biomarker for cellular integrity/density. Thus, in one aspect, disclosed herein is a biomarker for loss of cellular integrity/density and AD, wherein the biomarker is a surrogate measurement of tissue cellular density/integrity, $\Delta R2t^*$, obtained from gradient echo MRI (e.g., GEPCI) measured in the hippocampus of the brain.

Gradient Echo Plural Contrast Imaging (GEPCI) technique provides quantitative in vivo high resolution 3D measurements of several brain-tissue-specific relaxation properties of the gradient recalled echo (GRE) MRI signal. GEPCI is a combination of GRE sequence with multiple gradient echoes (and with different attributes, like navigator echo, fat suppression, etc.) AND a model for data analysis that allows extraction of several tissue specific parameters characterizing MRI signal ($R2^*$ and $R2t^*$ among others) and creating quantitative maps of these parameters in all brain regions. In short, GEPCI can be used to acquire and analyze MR images with multiple gradient echoes from a brain, and from this tissue-specific $R2^*$ and $R2t^*$ values can be calculated. Thus, in one aspect, disclosed herein are methods of measuring β-amyloid accumulation and/or cellular integrity/density loss in the brain of a subject wherein the gradient echo MRI is GEPCI.

In another aspect, disclosed herein are methods of detecting or diagnosing Alzheimer's Disease using the biomarkers and/or methods of measuring β-amyloid accumulation and/or loss of cellular integrity/density disclosed herein. Specifically, it is understood and herein contemplated that the loss of cellular integrity/density in the brain beyond simply atrophy is indicative that a subject has Alzheimer's disease. In one aspect disclosed herein are methods of diagnosing Alzheimer's disease comprising obtaining a scan of the brain of a subject using gradient echo magnetic resonance imaging (MRI) technique, measuring tissue specific $R2t^*$ values in specific brain regions (including hippocampus); wherein a decrease of $R2t^*$ in some specific brain regions relative to a normal control (i.e., decreased $\Delta R2t^*$) indicates that the subject has AD.

While loss of cellular integrity/density in the brain can be sufficient to diagnose AD, it is further contemplated herein that by measuring β-amyloid accumulation and cellular integrity, not only can a diagnosis of AD be made, but the a distinction can be made between a normal subject, a pre-clinical subject, and a clinical subject (including subject with mild clinical AD). Accordingly, disclosed herein are methods of diagnosing a subject with AD comprising obtaining a scan of the brain of a subject using gradient echo magnetic resonance imaging (MRI) technique, measuring tissue specific $R2^*$ values in specific brain regions (including, but not limited to precuneus, fusiform, lingual, paracentral, rostral-anterior cingulate, and parahippocampus)); measuring tissue specific $R2t^*$ values in specific brain regions (including hippocampus); wherein increased $\Delta R2^*$ is sensitive to early preclinical stages of AD and decreased $\Delta R2t^*$ indicates that subject has clinical AD. More specifically, disclosed herein are diagnostic methods wherein an increase in $R2^*$ values in $R2^*$ specific brain regions relative to a normal control (i.e., increased $\Delta R2^*$) and equivalent $R2t^*$ in $R2t^*$ specific brain regions relative to a normal control ($\Delta R2t^*$ approximately 0) indicate that the subject has pre-clinical AD; and wherein an increase in $R2^*$ values in $R2^*$ specific brain regions relative to a normal control (i.e., increased $\Delta R2^*$) and a decrease in $R2t^*$ values in $R2t^*$ specific brain regions relative to a normal control (i.e., decreased $\Delta R2t^*$) indicates that the subject has clinical AD. In one aspect, the method can further comprise measuring the accumulation of tau proteins in the brain.

Measuring amyloid accumulation in the brain is currently performed using PET which is a very costly, time consuming and not wildly available modality. MRI is faster and wildly available modality—MRI scanners are present in practically any hospital in US and worldwide. The gradient echo MRI (e.g., GEPCI) scan that is disclosed herein can be performed on any MRI scanner. Even though the relationship between amyloid accumulation and $\Delta R2^*$ that was established and disclosed herein is valid only for 3T MRI, a similar relationship can be established for other field strength as well. Since this technique does not involve radiation (as PET does) and can be implemented on practically any MRI scanner, it can be widely used for patient diagnostic and clinical trials. Hence, the present disclosure provides a much less costly, much more available and much less invasive (no radiation is involved) method for measuring amyloid accumulation in the brain.

The GEPCI technique is mainly based on quantitative measurements of the tissue-specific transverse relaxation (R2*, i.e. 1/T2*) of the gradient echo MRI signal. Since this signal is affected by field inhomogeneities and physiological fluctuations, several methods were developed to deal with these adverse effects. Specifically, to account for the contribution of magnetic field inhomogeneities on transverse relaxation, a voxel spread function method was developed. This technique takes into account voxel spread function (VSF) effects and allowed obtaining virtually free from artifacts R2* maps for all simulated, phantom and in vivo data except of the edge areas with very steep field gradients.

In the presence of macroscopic magnetic field inhomogeneities in MR experiment, the signal from an imaging voxel can be represented in a general form as follows $$S(TE,\{p\})=S_0(TE,\{p\}) \cdot F(TE) \quad [1]$$

where $S_0(TE, \{p\})$ is a signal that would exist in the absence of macroscopic magnetic field inhomogeneities, $\{p\}$ is a set of parameters that characterize system under consideration, $F(TE)$ is a function that describes contribution to the signal from macroscopic magnetic field inhomogeneities and TE is a time after initial RF excitation pulse. For SE-based experiments it is often convenient to define time origin (TE=0) at a spin echo time.

VSF approach provides a tool for accounting for the macroscopic magnetic field inhomogeneities and calculating $F(TE)$ based on phase information provided by GEPCI data. This approach can be applied for analyzing MR signals describing by different models.

Fitting the Eq. [1] to experimental data on the voxel-by-voxel basis a map of parameters p can be created. Thus, in one aspect, disclosed herein are methods of diagnosing AD, measuring loss of cellular integrity/density in the brain, and measuring β-amyloid accumulation, further comprising using a voxel spread function method to account for the adverse effects of field inhomogeneities.

To account for artifacts related to physiological fluctuations another correction technique was developed. Navigator echoes were used to monitor and correct the $f_0$ fluctuations of main magnetic field B0. This procedure was similar to that used previously, but in the present approach the navigator was placed after all gradient echoes were acquired. First Inverse Fourier Transform was applied to the navigator signal ($k_x$-space) along the readout direction (x) to produce images projected on this direction. Then for each spatial point x of this image and each phase encoding step, the phase difference between the N-th ($\phi_N(x)$) and the first ($\phi_1(x)$) spatial encoding step was calculated. Finally, the correction was applied to each phase encoding step with gradient echo time TE. Accordingly, in one aspect, disclosed herein are methods of diagnosing AD, measuring loss of cellular integrity/density in the brain, and measuring β-amyloid accumulation, further comprising using navigator echoes to account for the adverse effects of physiological fluctuations.

$$S_N^c(x, TE) = S_N(x, TE) \cdot e^{-i\frac{\phi_N(x)-\phi_1(x)}{M \cdot \Delta TE}TE} \quad [14]$$

where $S_N^c(x,TE)$ and $S_N(x,TE)$ are the signals in k-space after and before correction, respectively. Here we assume that the frequency $f_0$ did not change during the short period of time when M consecutive gradient echoes were acquired. This procedure is applied to each RF channel independently.

It is understood and herein contemplated that the presence of deoxygenated blood changes the local magnetic field around and within the blood vessels creating inhomogeneous distribution of local frequency shifts of water molecules. As a result, a faster transverse decay rate (R2*) of MRI signal can be observed, i.e. BOLD (blood-oxygen-level dependent) effect. An advanced GEPCI method that is based on the model that takes into account BOLD effect was developed that provides additional information on brain hemodynamic properties such as the BOLD effect (i.e., oxygen extraction fraction (OEF)), deoxygenated cerebral blood volume (dCBV) and concentration of tissue deoxyhemoglobin ($C_{deoxy}$).

To include BOLD effect, the MR signal decay from an imaging voxel in a gradient echo experiment can be represented as a product of several factors:

$$S(TE)=S_0 \cdot \exp[-R2t^* \cdot TE + i \cdot 2\pi \cdot \Delta f \cdot (TE-TE_1)] \cdot F_{BOLD}(TE) \cdot F(TE) \quad [2]$$

where TE is the gradient echo time, R2t* is the tissue-specific transverse relaxation rate constant (describing GEPCI signal decay in the absence of BOLD effect), $\Delta f$ is the frequency shift (dependent on tissue structure and also macroscopic magnetic field created mostly by tissue/air interfaces), function $F_{BOLD}(TE)$ describes GEPCI signal decay due to the presence of blood vessel network with deoxygenated blood (veins and adjacent to them part of capillaries), and function $F(TE)$ describes effect of macroscopic magnetic field inhomogeneities. Function $F_{BOLD}(TE)$ describes GRE signal decay due to the presence of blood vessel network with deoxygenated blood (veins and adjacent to them part of capillaries):

$$F_{BOLD}(TE) = 1 - \frac{\zeta}{1-\zeta} \cdot f_s(\delta\omega \cdot TE) + \frac{1}{1-\zeta} \cdot f_s(\zeta \cdot \delta\omega \cdot TE) \quad [3]$$

Eq. [3] better accounts for the presence of large vessels in the voxel than traditional exponential function. In Eq.[3], $\zeta$ is volume fraction of magnetic susceptibility inclusions (i.e., the deoxygenated cerebral blood volume fraction (dCBV)) and $\delta\omega$ is the characteristic frequency determined by the susceptibility difference between deoxygenated blood and surrounding tissue:

$$\delta\omega = \frac{4}{3}\pi \cdot \gamma \cdot B_0 \cdot Hct \cdot \Delta\chi_0 \cdot (1-Y) \quad [4]$$

In this equation, $\Delta\chi_0=0.27$ ppm is the susceptibility difference between fully oxygenated and fully deoxygenated red blood cells, Y is the blood oxygenated level (with Y=0 being fully deoxygenated blood), Hct is the blood hematocrit, and $\gamma$ is the gyromagnetic ratio. The non-linear function $f_s$, describes the signal decay due to the presence magnetic susceptibility inclusions which can account for inclusions such as blood vessel network (BOLD effect). The following mathematical expression can be used for the function $f_s$ in terms of a generalized hypergeometric function $_1F_2$:

$$f_s(\delta\omega \cdot TE) = {}_1F_2\left(\left[-\frac{1}{2}\right]; \left[\frac{3}{4}, \frac{5}{4}\right]; -\frac{9}{16}(\delta\omega \cdot TE)^2\right) - 1 \quad [5]$$

By fitting equation [2] to the complex signal using non-linear regression algorithm, the five parameters were identified: $S_0$, R2t*, $\Delta f$, $\zeta$ and $\delta\omega$ for each voxel in the brain.

Based on the fitting results Oxygen Extraction Fraction (OEF) can be calculated $$OEF = 1 - Y = \delta\omega \cdot (\tfrac{4}{3}\pi \cdot \gamma \cdot B_0 \cdot Hct \cdot \Delta\chi_0)^{-1} \quad [6]$$

and the concentration of deoxyhemoglobin per unit tissue volume:

$$C_{deoxy} = \frac{3}{4} \cdot \frac{\zeta \cdot \delta\omega \cdot n_{Hb}}{\gamma \cdot \pi \cdot \Delta\chi_0 \cdot B_0} \quad [7]$$

where $n_{Hb}$ is the total intracellular Hb concentration equal to $5.5 \times 10^{-6}$ mol/mL.

Thus, also disclosed herein are methods of diagnosing AD, measuring loss of cellular integrity/density in the brain, and measuring β-amyloid accumulation, further comprising accounting for oxygen extraction fraction, deoxygenated cerebral blood volume, and the concentration of tissue deoxyhemoglobin.

It is understood and herein contemplated that controls can be used in the disclosed methods and values determined relative to controls. Thus, in one aspect, disclosed herein are methods of diagnosing AD in a subject, comprising obtaining a scan of the brain of a subject using gradient echo plural contrast imaging (GEPCI) magnetic resonance imaging (MRI), measuring tissue specific R2* values, calculating the tissue specific ΔR2* (difference between subject's R2* value and age-adjusted value for healthy control subject) values in these specific areas of the brain; wherein an increase in tissue specific ΔR2* indicates that the subject has AD.

Given the usefulness and significant advantages of using GEPCI for the diagnosis of AD, as well as, the calculations paramount to the correlation of ΔR2* with amyloid accumulations, it is recognized herein that what is useful in the medical field is a system for diagnosing AD and/or measuring β-amyloid accumulation. Thus, in one aspect, disclosed herein are systems for measuring amyloid concentration (i.e., accumulation) in the brain comprising an MRI device, a processor for determining the ΔR2* and a display. Similarly, because decreases in ΔR2t* directly correlate with loss of cellular integrity/density in the brain and the loss of cellular integrity/density in the brain is indicative of AD, it is recognized that also useful in the medical field is a system for AD and/or measuring cellular integrity/density. Accordingly, in one aspect, disclosed herein are systems for measuring loss of tissue cellular density/integrity in the brain comprising an MRI device; a processor for determining the ΔR2t* in specific regions of the brain and the phenomenological relationship between ΔR2t* and loss of tissue cellular density/integrity, and a display. In one aspect, the system for measuring β-amyloid accumulation and measuring loss of tissue cellular density/integrity in the brain are part of the same system. Thus, in one aspect, disclosed herein are systems for diagnosing AD comprising an MRI device; a processor for determining the R2* and R2t* in regions of the brain, a phenomenological relationship between ΔR2* and ΔR2t* in regions of the brain, and severity of Alzheimer's disease; and a display. The processor for determining the ΔR2* and ΔR2t* can be the same or different processors. In one aspect, disclosed herein are systems wherein the processor for determining the ΔR2t* and the ΔR2* are the same processor.

It is also contemplated herein that the systems for diagnosing AD can also be utilized for distinguishing normal, pre-clinical AD, and clinical AD (e.g., mild AD). Thus, in one aspect, disclosed herein are systems for diagnosing Alzheimer's disease comprising an MRI device; a processor for determining a combination of GEPCI surrogate markers of β-amyloid burden, ΔR2*, and tissue cellular loss/integrity, ΔR2t*; a processor for distinguishing between normal, preclinical AD, and mild AD groups; and a display. As with other systems disclosed herein, the processor for determining the combination of GEPCI surrogate markers and the processor for distinguishing normal, pre-clinical AD, and clinical AD (e.g., mild AD) can be on the same or different processors. In one aspect, disclosed herein are systems wherein the processor for determining the combination of GEPCI surrogate markers and the processor for distinguishing normal, pre-clinical AD, and clinical AD (e.g., mild AD) are the same processor.

It is understood and herein contemplated that accurate assessment of tissue specific ΔR2* can benefit from the ability to account for field inhomogeneities, physiological fluctuations and additional brain structural and functional information. These additional calculations are appropriately addressed by the processor in the system. Accordingly, and in one aspect, disclosed herein are AD diagnostic systems wherein the processor further accounts for the contribution of magnetic field inhomogeneities on transverse relaxation, artifacts related to physiological fluctuations, and effects of oxygen extraction fraction, deoxygenated cerebral blood volume, and/or the concentration of tissue deoxyhemoglobin.

The present disclosure provides methods of detection and diagnosis of Alzheimer's disease by measuring tissue specific MRI signal relaxation rate parameters R2* and R2t*, and creates R2* and R2t* image contrast in MRI using gradient echo imaging. In accordance with the present disclosure, the influence of magnetic field inhomogeneities on MRI signals can be removed by making use of a unique signal post-processing procedure. In one aspect, the influence of physiological fluctuations on MRI signals can be removed by making use of a unique signal post-processing procedure in combination with a specially designed MRI pulse sequence.

As stated herein, the techniques disclosed herein are based on multi-gradient-echo approach and allows obtaining R2* and R2t* contrast images in MRI. Through use of the present invention, both R2* and R2t* as well as T1 weighted contrast images can be obtained in a single scan. All such images will also be naturally co-registered which is particularly advantageous for clinical applications.

The methods disclosed herein can be implemented using either two dimensional or three dimensional pulse sequences and since relatively low flip angles are used, the present invention requires substantially less RF power than SE acquisition techniques. A half-Fourier approach can be applied to increase the speed of the acquisition further. A parallel image acquisition approaches can also be applied to increase the speed of the acquisition further. A magnetization preparation block can also be used to suppress lipid or CSF signals, to enhance T1 contrast and reduce partial volume effects.

In one aspect, the methods of acquiring MR images disclosed herein can include determining a nonlinear function of gradient echo time to offset magnetic field inhomogeneities. Multiple sets of MR data are acquired from a series of read-out gradients in a pulse sequence. The invention also includes fitting non-linear theoretical model to experimental data to obtain tissue specific MRI signal relaxation rate parameters R2* and R2t* and then creating R2*, R2t* and T1 weighted images using the results of the fitting step.

In accordance with another aspect of the invention, an MRI apparatus is disclosed to rapidly acquire R2*, R2t* and T1 weighted images that includes a magnetic resonance imaging (MRI) system having a plurality of gradient coils positioned about a bore of a magnet to impress a polarizing magnetic field. An RF transceiver system and an RF switch are controlled by a pulse module to transmit and receive RF signals to and from an RF coil assembly to acquire the MR images. The MRI apparatus can comprise a computer programmed to acquire multiple sets of MR data from a series of read-out gradient pulses in a pulse sequence and determine signal intensity for each MR data. The computer then fits the MR data to a signal magnitude equation that includes a nonlinear function, and then reconstructs T2 weighted MR images that are substantially free of magnetic field inhomogeneities.

In order to reconstruct the $R2^*$, $R2t^*$ and T1 weighted images, the method includes a computer program for use with an MRI apparatus that includes instructions which, when executed by a computer, cause the computer to apply a pulse sequence with a train of gradient read-out pulses and acquire MR data during the train of gradient read-out pulses. The program determines a model for nonlinear function of gradient echo time based on the object scanned and the physical characteristics of the MR apparatus. The program then fits theoretical model to the MRI data and reconstructs MR images using the results of the fit wherein the MR images reconstructed can include not only $R2^*$, $R2t^*$ and T1 weighted images, but also maps of oxygen extraction fraction (OEF), deoxygenated blood volume (dCBV) and tissue concentration of deoxyhemoglobin $C_{deoxy}$.

B. EXAMPLES

1. Example 1

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for.

GEPCI data was obtained from 20 healthy control subjects with a range of ages between 20 and 80 years old and used this data as a baseline measures of $R2^*$, i.e. $R2^*_H$. GEPCI $R2^*$ data was also acquired from another 20 subjects referred to us by WU Alzheimer Disease Research Center (ADRC) and their amyloid measurements (standard uptake value ratio (SUVR)$_{amyloid}$) were made available to us. These subjects' also had cognitive conditions evaluated using Clinical Dementia Rating (CDR) scores. Four subjects have CDR bigger than 0 (0.5 or 1). For each of these subjects and each area in the brain $\Delta R2^* = R2^* - R2^*_H$ was calculated. Some areas in the brain show very strong correlation between $\Delta R2^*$ and amyloid accumulation which can be expressed as a following relationship:

$$SUVR = a + k \cdot (R2^* - R2^*_H) \qquad [8]$$

where SUVR$_{amyloid}$ is a standard measure of amyloid concentration from PET used in the literature; phenomenological parameter "a" defines SUVR for subjects that have $\Delta R2^* = 0$; and phenomenological parameter "k" defines the slope of SUVR vs. $\Delta R2^*$ relationship showing change in SUVR per unit change of $\Delta R2^*$. Examples of such a correlation is shown in FIGS. 2 and 3 below. Measuring tissue specific $\Delta R2^*$ values in these specific areas of the brain provides MRI-based measurements of amyloid accumulation.

While a strong correlation between amyloid SUVR$_{amyloid}$ and $\Delta R2^*$ exists only in selected regions of the brain, a very strong correlation also exists between amyloid concentrations in different regions of the brain (except white matter) for each subject. A mathematical relationships was established describing these correlations. That means that by measuring amyloid concentration (using MRI) in the brain, for example, in the parahippocampal region of the brain, we can evaluate amyloid concentration in all other regions. FIGS. 2 and 3 below shows GEPCI-estimated vs. PET-measured amyloid SUVR in all subjects. In FIGS. 2 and 3 a very high correlation between these two measurements was observed, further supporting our claim that GEPCI can measure amyloid in the brain consistent with PET measurements. That is, a strong correlation was found between baseline-corrected GEPCI $R2^*$ measurements and PET SUVR$_{amyloid}$ measurements. This correlation allows the use of GEPCI $R2^*$ measurements to estimate amyloid accumulation.

2. Example 2: In Vivo Detection of Microstructural Correlates of Brain Pathology in Preclinical and Early Alzheimer Disease with Magnetic Resonance Imaging Alzheimer's disease (AD) is a neurodegenerative disorder that is characterized clinically by progressive dementia caused by pathological changes in brain tissue. Unfortunately, to date all "disease-modifying" experimental therapies for AD have not demonstrated clinical benefit in individuals with symptomatic AD. One possibility for these failures is that the drugs were administered too late in the course of the AD pathological process which likely begins 15-20 years prior to the onset of clinical symptoms. This preclinical stage of AD provides a large window for therapeutic intervention. Hence, one of the important directions in AD therapy is developing widely accessible biomarkers that can detect AD brain pathology at the clinically silent preclinical stages.

One of the prevailing hypothesis in the pathogenesis of AD is the amyloid cascade hypothesis suggesting that the abnormal accumulation of amyloid beta protein (Aβ) is one of the earliest pathological markers of AD. Paradoxically, it is also known that the medial temporal lobe (MTL) of the brain that plays an important role in human memory, is not the most affected region by the Aβ deposition compared with other cortical regions (e.g. prefrontal cortex and precunues). At the same time, histological studies indeed showed that MTL is particularly vulnerable to the neurofibrillary pathology in the early stage of AD. The reduction of volume and the loss of cells in the entorhinal cortex and hippocampus have been extensively reported in mild cognitive impairment (MCI) and AD subjects. Importantly, it was established by histology that the AD symptoms do not start until cellular loss occurs in the hippocampal area.

As disclosed herein, MRI is a powerful tool that can identify changes in the Alzheimer brain. Most MRI studies so far focused on AD-related volumetric measurements of brain atrophy. A few studies attempted directly identifying amyloid plaques in postmortem specimens or mice models, though the latter methods require long imaging time and have not been translated to human studies yet.

Herein, an MRI-based method was used allowing in vivo simultaneous detection of amyloid accumulation and cellular damage in humans with Alzheimer disease. The approach is based on the Gradient Echo Plural Contrast Imaging (GEPCI) technique developed in the lab and used in multiple sclerosis, psychiatric diseases and aging studies. The GEPCI technique provides quantitative in vivo high resolution 3D measurements of several brain-tissue-specific parameters of the gradient recalled echo MRI signal (GEPCI metrics). The GEPCI metrics depending on the molecular constituents of cell-building materials present in the brain can serve as surrogate markers reflecting disease-related tissue damage.

The data obtained on 34 participants demonstrate that GEPCI quantitative metrics significantly depend on amyloid accumulation and tissue damage. A remarkable correlation was uncovered between GEPCI metrics and PET-measured amyloid (current in vivo gold standard) in several MTL areas, thus validating GEPCI as a surrogate marker for amyloid imaging in preclinical and early Alzheimer disease. A significant correlation was also demonstrated between GEPCI surrogate marker of brain tissue (i.e., neuronal) cellular loss in the hippocampus and cognitive performance, thus validating GEPCI as a surrogate marker of brain tissue "health status". Importantly, the latter correlation is much stronger than the correlation between cognitive performance and hippocampal atrophy, thus indicating that the "health status" of the remaining tissue is more important parameter than the loss of tissue volume alone. As the recruited participants represented either healthy group or had a very mild or mild cognitive impairment, the results demonstrate high GEPCI sensitivity to early AD-related pathological changes in brain tissue. By combining both GEPCI surrogate markers of amyloid burden and neuronal loss normal, preclinical, and mild AD groups can be distinguished. Since the approach is based on MRI that is widely available worldwide, is non-invasive, and does not require radiation exposure, it can open opportunities for obtaining new information on the pathogenesis of one of the most devastating diseases of aging population—the Alzheimer disease. The new method can also open the door for screening population for early symptoms of AD pathology and clinical drug trials.

a) Results and Discussion

GEPCI technique is based on (i) 3D GRE MRI sequence with multiple gradient echoes (currently available from most MRI scanner manufacturers), (ii) theoretical model of GRE signal relaxation properties, and (iii) a set of post-processing algorithms allowing generating images and quantitative maps with several contrasts reflecting biological tissue anatomic, microstructural and functional properties. Importantly, all these GEPCI images are simultaneously acquired and thus, co-registered The theoretical model is broadly accented for GRE signal analysis. It was validated on phantoms and small animal model developed algorithms for correction adverse background field gradient effects and method for minimizing effects of physiological fluctuations.

The GEPCI technique mainly relies on the quantitative measurements of the transverse relaxation properties (T2*) of the Gradient Recalled Echo (GRE) MRI signal. The tissue MRI relaxation parameters measured by GEPCI depend on the cellular environment of water molecules—higher concentrations of proteins, lipids, iron, and other constituents of biological tissue and cell-building materials (sources of MR signal relaxation) lead to higher relaxation rate constants. Indeed, in a pure water or CSF, the R2* (=1/T2*) is about 1 $s^{-1}$, while in a normal brain tissue R2* is about 15-20 $s^{-1}$. A novel advanced approach that was developed allows to separate the total R2* relaxation into tissue-specific (R2t*) and BOLD (Blood-Oxygen-Level-Dependent) contributions. Since R2t* describes the part of the signal decay resulting from water molecules interaction with cellular components of biological tissues, it is sensitive to cellular alterations in human brain.

In the context of the AD, increased amyloid deposition leads to the increased GEPCI metrics, especially R2* that is sensitive to mesoscopic field inhomogeneities that can be present around amyloid deposits and can be enhanced due to iron presence in amyloid plaques. On the other hand, cellular loss characteristic to AD can lead to decreased GEPCI metrics, especially R2t* that is a surrogate marker of the cellular density. The interplay between these two opposed processes can define important features of GEPCI signal in AD.

Herein, only participants either without any AD symptoms or with very mild and mild cognitive impairment where AD-related pathology is known to occur mainly in the MTL were included. Changes that were found in the GEPCI metrics are also located mostly in the MTL.

(1) Correlation Between R2* and PET Aβ Measurement

The correlation analysis between GEPCI measurements of R2* relaxation rate constant and amyloid PET measurements (using PiB standardized uptake value ratio [SUVR]) revealed positive correlations in most cortical brain regions. The data show significant correlations not only in the areas of high Aβ accumulation (e.g. precuneus) but also in the areas of MTL, such as the parahippocampal cortex and the fusiform cortex. While most brain regions demonstrated positive correlation between GEPCI R2* and PET amyloid SUVR, not all correlations were statistically significant after correction for multiple comparison using false discovery rate (FDR), most likely due to the small sample size (PiB data were available only for 19 participants). Examples of the correlations with significant n values are shown in FIG. 4

The strongest correlation between GEPCI R2* and Aβ SUVR in parahippocampal cortex shows sensitivity of GEPCI R2* to Aβ accumulation in this area. Interestingly, although the range of SUVR in parahippocampal cortex was smaller than in precuneus, the correlation in parahippocampal cortex was much stronger than that in precuneus. It indicates that even though MTL is not the area of the highest burden of Aβ in the AD brain, it represents the most important area of pathological changes in early AD, particularly as it relates to the formation of Aβ plaques in the cerebral cortex, where the changes can be detected by GEPCI R2*. This feature can be attributed to distinct cellular properties of the gray matter in the MTL that play important roles in functionally connecting the neocortex and hippocampus. Structurally, the parahippocampal gyrus is a transitional zone, where the entorhinal cortex (referred as perialocortex) contains the lamina dissecans while the perirhinal and parahippocampal cortexes (referred as proisocortex) have their cellular structure different from the major three-layered and six-layered cortex areas. As different cellular components and arrangements contribute to R2*, it is possible that the strong correlations between R2* and Aβ SUVR in the parahippocampal cortex is due to its unique laminar organizations. Since the medial portion of the fusiform gyms is also considered to be part of the parahippocampal cortex, it is reasonable to see the significant correlation between R2* and Aβ SUVR in the fusiform as well.

The presence of neurofibrillary tangles (NFTs) and neuronal loss in the parahippocampal gyms can also affect R2* measurements. However, their participants were assessed at death after nearly a decade of dementia, while the cohort disclosed herein represents mostly normal, pre-symptomatic, very mild (CDR=0.5) or mild (CDR=1) AD. In addition, as tissue damage in the parahippocampal gyrus was smaller than that in the hippocampus, in this cohort the loss of neurons in the parahippocampal gyms may not be severe enough to affect the R2* measurements.

Even though the strong correlations between R2* and Aβ SUVR was seen only in a few brain regions, the R2* measurements can still be used for evaluation of Aβ burden in all multiple regions. Indeed, the data show very strong correlations between Aβ SUVR in most cortical regions and the R2* values in the parahippocampal cortex. These correlations can be described as follows:

$$SUVR = a + k \cdot (R2^* - \overline{R2}_H^*) \qquad [9]$$

where $\overline{R2}_H^*$ is the mean value of R2* in the parahippocampal cortex of the normal control group (9 participants with negative PiB Aβ and CDR=0). The $\overline{R2}_H^*$ is introduced in Eq. [9] to make the coefficients a more meaningful—they represent region-specific average SUVR for healthy control group. The coefficients of the linear regression (a and k in Eq. [9]) and the results of the correlation analysis are presented in Table 1.

TABLE 1

Results of linear regression analysis of the relationship between regional amyloid SUVR in different cortical regions and the parahippocampal R2*

| Cortical area | Intercept (a) | Slope (k, sec) | p value | r |
|---|---|---|---|---|
| bankssts | 1.35 | 0.24 | 2.47E−04 | 0.75 |
| caudal-anteriorcingulate | 1.23 | 0.27 | 2.45E−04 | 0.75 |
| caudal-middlefrontal | 1.16 | 0.24 | 1.76E−04 | 0.76 |
| cuneus | 1.22 | 0.12 | 2.79E−02 | 0.50 |
| entorhinal | 1.10 | 0.08 | 1.33E−04 | 0.77 |
| frontalpole | 1.07 | 0.30 | 5.31E−04 | 0.72 |
| fusiform | 1.21 | 0.15 | 2.02E−04 | 0.75 |
| inferiorparietal | 1.21 | 0.23 | 4.08E−04 | 0.73 |
| inferiortemporal | 1.15 | 0.20 | 4.63E−04 | 0.72 |
| insula | 1.23 | 0.18 | 2.90E−04 | 0.74 |
| isthmuscingulate | 1.34 | 0.25 | 5.46E−04 | 0.72 |
| lateraloccipital | 1.15 | 0.12 | 1.22E−03 | 0.68 |
| lateralorbitofrontal | 1.26 | 0.25 | 4.45E−04 | 0.72 |
| lingual | 1.19 | 0.12 | 6.46E−03 | 0.60 |
| medialorbitofrontal | 1.23 | 0.32 | 2.98E−04 | 0.74 |
| middletemporal | 1.13 | 0.21 | 1.73E−04 | 0.76 |
| paracentral | 1.21 | 0.23 | 1.00E−03 | 0.69 |
| parahippocampal | 1.11 | 0.15 | 6.09E−06 | 0.84 |
| parsopercularis | 1.19 | 0.23 | 4.66E−04 | 0.72 |
| parsorbitalis | 1.13 | 0.26 | 4.97E−04 | 0.72 |
| parstriangularis | 1.20 | 0.24 | 3.90E−04 | 0.73 |
| pericalcarine | 1.27 | 0.14 | 2.56E−02 | 0.51 |
| postcentral | 1.07 | 0.15 | 2.02E−03 | 0.66 |
| posteriorcingulate | 1.29 | 0.32 | 4.58E−04 | 0.72 |
| precentral | 1.14 | 0.14 | 9.57E−04 | 0.70 |
| precuneus | 1.30 | 0.32 | 5.93E−04 | 0.71 |
| rostralanteriorcingulate | 1.23 | 0.31 | 2.28E−04 | 0.75 |
| rostralmiddlefrontal | 1.16 | 0.30 | 4.34E−04 | 0.73 |
| superiorfrontal | 1.14 | 0.28 | 3.25E−04 | 0.74 |
| superiorparietal | 1.15 | 0.21 | 6.31E−04 | 0.71 |
| superiortemporal | 1.15 | 0.18 | 2.45E−04 | 0.75 |
| supramarginal | 1.16 | 0.21 | 6.68E−04 | 0.71 |
| temporalpole | 1.11 | 0.10 | 9.94E−04 | 0.69 |
| transversetemporal | 1.21 | 0.18 | 4.48E−04 | 0.72 |

Cortical regions are selected based on the FreeSurfer segmentation. The data show coefficients of linear regression (Eq. [2]) and the correlation coefficients (r). The mean value of R2* in the parahippocampal region for the control group in Eq. [2] is 16.55 sec⁻¹.

The slopes of the regression (parameter k in Eq. [8] and [9]) are also shown in FIG. 5, upper row. The spatial pattern in FIG. 5 is similar to previously established correlation pattern between regional and mean values of PiB SUVR. Hence, the data demonstrate that the R2* measurements in the MTL (especially the parahippocampal cortex) not only correlate with amyloid PET measurements in this area but also strongly correlate with amyloid PET measurements throughout the entire cortex.

While the data show rather significant positive correlations between R2* and amyloid burden across the participants in different brain regions (FIG. 4), there also exists an inverse association across the brain regions between averaged R2* and amyloid distributions. FIG. 5 shows mean values of R2* and Aβ SUVR averaged across 19 participants mapped onto the brain surface. Lower R2* are found in the frontal cortex, posterior cingulate, precuneus, parahippocampal cortex, entorhinal cortex and superior temporal cortex. Higher R2* are found in the occipital cortex, paracentral cortex, fusiform, middle and inferior temporal cortex. This R2* distribution is consistent with the previous studies. In contrast to the R2*, the PiB retention was prominently higher in the frontal cortex, posterior cingulate, precuneus and inferior parietal cortex, which is also consistent with the previous reports. Generally speaking, PiB Aβ binding tends to increase in the regions with lower R2*, which may indicate that the regions with lower R2* are more vulnerable to the amyloid accumulation. This relationship is seen on the map in the frontal cortex, posterior cingulate, precuneus, inferior parietal cortex characterized with higher SUVR but lower R2*, and occipital cortex with lower SUVR but higher R2*.

Interestingly, the former regions mostly overlap the default mode network and tend to be both structurally and functionally vulnerable in normal aging and Alzheimer's disease, which was suggested to be due to a high degree of life-long plasticity. The R2*-Aβ association points to an important relationship between brain microstructural properties reflected in tissue specific R2* measurements and the relationships between default activity, amyloid, and memory. It is also in agreement that the cortical areas with lower R2t* (e.g. prefrontal cortex) may have more complex dendritic and synaptic structure, which may also be related to the neuroplasticity and AD vulnerability. From this perspective, the parahippocampal and entorhinal cortices, which are primary memory-related areas and are vulnerable to early Alzheimer, are also characterized by a lower baseline R2*. However, PiB retention and Aβ accumulation in these areas are not prominent. Nevertheless, the correlation between GEPCI R2* metrics and PiB retention in these areas is exceptionally strong, especially in the parahippocampal gyms.

(2) R2* Provides Differentiation Between Normal and Preclinical AD Participants

Strong correlations were uncovered between GEPCI R2* and PET PiB measurements in 19 participants (see correlation plot in FIG. 4). Since early AD is associated with Aβ accumulation, this indicates that the R2* can be used to differentiate between Aβ positive and Aβ negative brains. Indeed, FIG. 6 shows statistically significant differences based on R2* measurements in the parahippocampal cortex between amyloid negative and positive groups of the 34 participants (recall that two CDR positive participants were Aβ negative). The bar graph on the left in FIG. 6 shows a significant difference in the parahippocampal R2* between all participants (independent of CDR) with negative (n=15) and positive (n=19) Aβ status (see definition in the Methods). The bar graph on the right shows significant differences between normal group (CDR=0, amyloid negative, n=13) and preclinical group (CDR=0, Aβ positive, n=10).

(3) Correlation Between R2t* and Cognitive Performance Tests

GEPCI-derived tissue specific structural and functional metrics show that the parameter R2t* is related to the tissue neuronal density. Since the participants were characterized either as cognitively normal or having mild cognitive impairment (MCI), very few differences were found in their R2t* in most brain areas with the exception of the hippocampus. Importantly, the hippocampal R2t* correlated significantly with cognitive performance (FIG. 7), which is not surprising because a decreased R2t* in the hippocampus is related to decreased neuronal density. As presented in the scatter plots in FIG. 7, the hippocampal R2t* was associated with the free recall condition of the Free and Cued Selective Reminding Test (Srtfree; r=0.53, p=0.002), with the total correct score from the Animal Naming test (ANIMALS; r=0.50, p=0.0025), and with the Trailmaking Test Part A completion time (Tma; r=−0.47, p>0.017).

Note that considerably weaker correlations were found between hippocampal volume and cognitive performance (FIG. 7, second column), indicating that the integrity of the remaining hippocampal tissue (characterized by R2t*) is a more important parameter of hippocampal pathology than hippocampal volume.

No significant correlation was found between cognitive performance and R2* or CSF $A\beta_{42}$. This result is in agreement with the dissociation between PiB defined $A\beta$ plaques and cognitive performance. At least 30% of people with significant $A\beta$ burden are cognitively normal.

(4) R2t* Provides Differentiation Between Cognitively Normal and Mild AD Groups

To evaluate the efficiency of GEPCI surrogate biomarkers to distinguish between normal brain, preclinical AD, and mild AD cases participants were separated into three categories: normal brain (negative $A\beta$, no cognitive impairment), preclinical AD (positive $A\beta$, no cognitive impairment), and mild AD (positive $A\beta$, very mild dementia). Cognitive status is classified by the clinical dementia rating (CDR). No cognitive decline is characterized by the CDR=0, mild cognitive decline is defined by CDR=0.5 or 1. Amyloid positivity is defined by a cutoff of mean cortical Binding Potential (MCBP)=0.18 which corresponds to a mean cortical standardized uptake value ratio (MC-SUVR) of 1.3 referenced to cerebellar grey matter. MC-SUVR for $A\beta$ imaging is calculated as the average of regions within the prefrontal cortex, gyrus rectus, lateral temporal, and precuneus regions.

The bar graphs in FIG. 8 show group comparisons based on the R2t* results obtained in the hippocampus (results summarized in Table 2). The first box shows results for tissue R2t* and the second block shows results for hippocampal volume. The significantly decreased hippocampal volume in mild AD group is in agreement with known brain atrophy characteristic for AD.

TABLE 2

The mean and standard deviations of R2t* volume and TCI in hippocampus over three groups presented in FIG. 8

|  | R2t*(s⁻¹) | Volume(mm³) | TCI |
|---|---|---|---|
| Normal | 11.71 ± 1.45 | 3512 ± 327 | 0.00 ± 0.16 |
| Preclinical | 12.20 ± 1.50 | 3720 ± 452 | 0.11 ± 0.22 |
| Mild AD | 9.94 ± 1.38 | 2849 ± 552 | −0.31 ± 0.16 |

Where R2t* is related to neuronal density/integrity, the product of R2t* and the hippocampal volume (V) can characterize the total neuronal content in the hippocampus. Hence, to characterize the global tissue change in the hippocampus, it is convenient to introduce the Tissue Content Index (TCI):

$$TCI = \frac{(V \cdot R2t^*) - (V \cdot R2t^*)_{control}}{(V \cdot R2t^*)_{control}} \quad [10]$$

where $(V \cdot R2t^*)_{control}$ is a mean value of tissue content in the group of normal participants. The changes in the TCI between Normal, Preclinical and AD groups are shown in the third box of FIG. 8.

While changes in R2t* reflects changes in the neuronal and synaptic density, it can also reflect changes in other tissue components. A small (not significant) increase in tissue R2t* seen in preclinical group as compared to normal participants may be attributed to accumulation of tau protein as in early Braak stages of AD. Interestingly, the hippocampal volume in the preclinical group was also slightly (not significant) higher than in the normal group.

The results in FIG. 8 (hippocampal data) show that not only is the hippocampal tissue volume reduced in mild AD participants, but the tissue specific R2t* value is also reduced. It is not surprising that the TCI representing the product of the volume and R2t*, is reduced even more significantly. These results are in a full agreement with the histopathological studies where it was observed that 46% of neurons were lost in the hippocampus of people with CDR=0.5 as compared to cognitively normal participants, while the hippocampal volume loss was only 29%. Comparison of the findings herein with direct neuronal measurements further confirms the relationship between R2t* and neuronal density. The decreased R2t* and TCI is consistent with decreased tissue neuronal density and the tissue neuronal content in the hippocampus. Furthermore, no significant differences in hippocampal R2t*, volume and TCI between the normal and preclinical AD groups, is also consistent the histopathological finding of no significant difference in hippocampal neuron number and volume between the normal and preclinical AD groups.

b) Conclusion

Herein it was demonstrated that the GEPCI technique provides a new approach to the in vivo evaluation of pathology in the preclinical and early symptomatic stages of AD. It is based on a multi-gradient-echo MRI sequence that is available from most MRI manufacturers. GEPCI data are quantitative, reproducible and MRI scanner independent, thus allowing multi-center applications. The results show that GEPCI metrics are good correlates of $A\beta$ accumulation and neurodegeneration. They are sensitive enough to distinguish between normal individuals and those with preclinical (asymptomatic) and early symptomatic AD.

One of the significant finding is that the hippocampal tissue cellular integrity is a more important parameter affecting cognitive performance than hippocampal atrophy. Another important finding is that the AD symptoms do not start until there has been significant cellular loss in the hippocampus.

Since MRI is a much more available modality than PET (current imaging "gold standard" for in vivo quantifying AD ($A\beta$) brain pathology), and poses fewer risks, GEPCI metrics (R2* and R2t*) can improve the quality of AD diagnostic measures, patient care, patient outcome and the evaluation of new disease-modifying therapies.

c) Methods
(1) Subjects

This study was approved by the Institutional Review Board of Washington University School of Medicine (WUSM). 34 participants were selected from the studies of aging and dementia at the Knight Alzheimer's Disease Research Center (ADRC) at WUSM. All participants provided informed consent. Cognitive status was operationalized with the Clinical Dementia Rating (CDR), as determined by Knight ADRC clinicians according to standard protocols; diagnoses were in accordance with standard criteria. The participants were assessed to be cognitively normal (CDR=0) or to have mild (CDR=0.5 or 1) AD dementia. All participants in this study underwent a collection of cognitive performance tests, including Free and Cued Selective Reminding Test (Srtfree), Animal Naming (ANIMALS), and Trail making Test Part A (Tma). CSF biomarker $A\beta_{42}$ (INNOTEST, Fujirebio, Gent, Belgium) was available for 31 participants. 19 participants underwent PiB PET imaging to estimate amyloid deposition in their brains. According to the $A\beta$ status (see below), cognitively normal participants (CDR=0) were divided into normal (CDR=0; $A\beta$ negative) and preclinical (CDR=0; $A\beta$ positive) groups. Demographic information for all groups is presented in Table 3. For participants that underwent PET amyloid imaging, amyloid positivity was defined by a cutoff of mean cortical binding potential (MCBP)=0.18 which corresponds to a mean cortical standardized uptake value ratio (MC-SUVR) of 1.3 referenced to cerebellar grey matter. MC-SUVR for $A\beta$ imaging is calculated as the average of regions within the prefrontal cortex, gyrus rectus, lateral temporal, and precuneus regions. For participants that did not have PET $A\beta$ measurements, $A\beta$ positivity was determined by the status of their CSF biomarker $A\beta_{42}$. One participant with CDR=0.5 and one with CDR=1 had negative $A\beta$ status.

TABLE 3

Distribution of participants between groups and their demographic information.

| | Normal CDR = 0 $A\beta$ negative | Preclinical AD CDR = 0 $A\beta$ positive | Mild AD CDR = 0.5 or 1 |
|---|---|---|---|
| N | 13 | 10 | 11 (7/4) |
| Age | 69.6 ± 8.7 | 72.3 ± 8.4 | 76.0 ± 8.4 |
| Female/Male | 7/6 | 4/6 | 3/8 |

Note that nine participants in Mild AD group were $A\beta$ positive and two were $A\beta$ negative.

(2) Data Acquisition

All subjects were scanned in a 3T PET-MR scanner (Siemens, Erlangen, Germany). A 3D multi gradient echo sequence was used to obtain the data. Sequence parameters were: resolution 1×1×2 mm³ (read, phase, slab), FOV 256 mm×192 mm, repetition time TR=50 ms, flip angle 30°, 10 gradient echoes with first gradient echo time $TE_1$=4 ms, echo spacing $\Delta TE$=4 ms. Additional phase stabilization echo (the navigator data) was collected for each line in k-space to correct for image artifacts due to the physiological fluctuations. The total acquisition time of GEPCI is 11 mins 30s. Macroscopic field inhomogeneity effects (background gradients) were accounted for by using the voxel spread function (VSF) method. Standard clinical Magnetization-Prepared Rapid Gradient Echo (MPRAGE) images with TR/TI/TE=2200/1100/3.37 ms and the resolution 1×1×1 mm³ were also collected for segmentation purposes. The total acquisition time of MPRAGE is 6 mins. After the data acquisition, the raw k-space data were read into MATLAB (The MathWorks, Inc.) for the post-processing.

(3) Data Analysis and GEPCI Images Generation

After data acquisition, raw k-space data are read into MATLAB (The MathWorks, Inc.) for post-processing using algorithms. In brief, after correcting the k-space data for physiological artifacts, FFT was applied to get images. 3D spatial Hanning filter is then applied to the data in the image domain to reduce Gibbs ringing artefacts and increase signal-to-noise ratio (SNR) in the data. The multi-channel data are combined using the following algorithm:

$$S_n(TE) = \sum_{ch=1}^{M} \lambda_{ch} \cdot \overline{S}_n^{ch}(TE_1) \cdot S_n^{ch}(TE); \lambda_{ch} = \frac{1}{M \cdot \varepsilon_{ch}^2} \sum_{ch'=1}^{M} \varepsilon_{ch'}^2 \quad [11]$$

where the sum is taken over all M channels (ch), $\overline{S}$ denotes complex conjugate of S, $\lambda_{ch}$ are weighting parameters and $\varepsilon_{ch}$ are noise amplitudes (r.m.s.). Index n corresponds to the voxel position (n=x,y,z). This algorithm allows for the optimal estimation of quantitative parameters, and also removes the initial phase incoherence among the channels.

Standard R2*=1\T2* values are estimated by fitting the following equation to experimental data:

$$S(TE) = A_0 \cdot \exp(-R2^* \cdot (TE+TE_1) + i \cdot 2\pi \cdot \Delta f \cdot (TE-TE_1) \cdot F(TE) \quad [12]$$

where TE is the gradient echo time, $\Delta f$ is the frequency shift (dependent on tissue structure and also macroscopic magnetic field created mostly by tissue/air interfaces), and function F(TE) describes the effects of macroscopic magnetic field inhomogeneities. A voxel spread function (VSF) method was used for calculating F(TE).

To separate contributions of tissue-specific (R2t*) and susceptibility effects to the total R2* relaxation, the model below was used:

$$S(TE) = A_0 \cdot \exp[-R2t^* \cdot (TE+TE_1) \cdot \zeta \cdot f_s(\delta\omega \cdot TE) + i \cdot 2\pi \cdot \Delta f \cdot (TE-TE_1)] \cdot F(TE) \quad [13]$$

where $\zeta$ is the volume fraction of magnetic susceptibility inclusions, $\delta\omega$ is the characteristic frequency determined by the susceptibility difference between inclusions and surrounding tissue, and non-linear function $f_s$, describes the signal decay due to the presence of magnetic susceptibility inclusions. This model can account for different types of inclusions, e.g. blood vessel network (BOLD effect), trabecular bone, iron oxide nanoparticles, etc.

Since no correlation exists between amyloid accumulation and BOLD effect, the correlation between amyloid accumulation and R2*, that was found in AD patients, is mostly related to magnetic susceptibility effects created by amyloid plaques. Iron deposition in amyloid plaques could lead to additional sensitivity of GEPCI R2* to $A\beta$ accumulation.

In this application focus was on total R2* and tissue specific R2t* measurements for quantifying tissue microstructural properties and GEPCI T1W images (the square root of parameter $A_0$ in Eqs. [3], [4]) for brain structure delineation and segmentation. The hemodynamic analysis is not part of this study.

(4) Image Segmentation.

FreeSurfer software (Laboratory for Computational Neuroimaging, Martinos Center for Biomedical Imaging) is used to generate brain segmentations, calculate surfaces, cortical thicknesses and volumes based on MPRAGE images. Then, MPRAGE images are registered to GEPCI-T1-weighted (T1W) images using FMRIB's Linear Image Registration Tool in FSL and the transformation matrices of the registration are generated. Finally, these matrices are applied to the brain segmentations from FreeSurfer and transformed to the space of GEPCI-T1W images. One of the important advantages of GEPCI is that all GEPCI images are generated from a single MRI scan and are naturally co-registered. Hence, segmentations of GEPCI T1W images are naturally co-registered with all other GEPCI maps.

To minimize the partial volume effect a CSF mask was applied to remove CSF signals. To maximize accuracy of measurements statistical results were reported instead of voxel-wise analysis: for each FreeSurfer region (usually containing thousands of voxels), a single parameter was generated—median value of GEPCI parameter which is less sensitive to outliers that are related to partial volume and other effects.

C. REFERENCES

Albert M S, DeKosky S T, Dickson D, Dubois B, Feldman H H, Fox N C, Gamst A, Holtzman D M, Jagust W J, Petersen R C, Snyder P J, Carrillo M C, Thies B, Phelps C H. The diagnosis of mild cognitive impairment due to Alzheimer's disease: Recommendations from the National Institute on Aging-Alzheimer's Association workgroups on diagnostic guidelines for Alzheimer's disease. Alzheimer's & Dementia 2011; 7(3):270-279.

Arnold S E, Hyman B T, Flory J, Damasio A R, Van Hoesen G W. The topographical and neuroanatomical distribution of neurofibrillary tangles and neuritic plaques in the cerebral cortex of patients with Alzheimer's disease. Cereb Cortex 1991; 1(1):103-116.

Bateman R J, Xiong C, Benzinger T L, Fagan A M, Goate A, Fox N C, Marcus D S, Cairns N J, Xie X, Blazey T M, Holtzman D M, Santacruz A, Buckles V, Oliver A, Moulder K, Aisen P S, Ghetti B, Klunk W E, McDade E, Martins R N, Masters C L, Mayeux R, Ringman J M, Rossor M N, Schofield P R, Sperling R A, Salloway S, Morris J C, Dominantly Inherited Alzheimer N. Clinical and biomarker changes in dominantly inherited Alzheimer's disease. The New England journal of medicine 2012; 367(9):795-804.

Benveniste H, Einstein G, Kim K R, Hulette C, Johnson G A. Detection of neuritic plaques in Alzheimer's disease by magnetic resonance microscopy. Proceedings of the National Academy of Sciences 1999; 96(24):14079-14084.

Benzinger T L, Blazey T, Jack C R, Jr., Koeppe R A, Su Y, Xiong C, Raichle M E, Snyder A Z, Ances B M, Bateman R J, Cairns N J, Fagan A M, Goate A, Marcus D S, Aisen P S, Christensen J J, Ercole L, Hornbeck R C, Farrar A M, Aldea P, Jasielec M S, Owen C J, Xie X, Mayeux R, Brickman A, McDade E, Klunk W, Mathis C A, Ringman J, Thompson P M, Ghetti B, Saykin A J, Sperling R A, Johnson K A, Salloway S, Correia S, Schofield P R, Masters C L, Rowe C, Villemagne V L, Martins R, Ourselin S, Rossor M N, Fox N C, Cash D M, Weiner M W, Holtzman D M, Buckles V D, Moulder K, Morris J C. Regional variability of imaging biomarkers in autosomal dominant Alzheimer's disease. Proceedings of the National Academy of Sciences of the United States of America 2013; 110(47):E4502-4509.

Braak H, Braak E. Frequency of stages of Alzheimer-related lesions in different age categories. Neurobiology of aging 1997; 18(4):351-357.

Braak H, Braak E. Neuropathological stageing of Alzheimer-related changes. Acta neuropathologica 1991; 82(4):239-259.

Braak H, Braak E. Staging of Alzheimer's disease-related neurofibrillary changes. Neurobiology of aging 1995; 16(3):271-278; discussion 278-284.

Braak H, Thal D R, Ghebremedhin E, Del Tredici K. Stages of the pathologic process in Alzheimer disease: age categories from 1 to 100 years. J Neuropathol Exp Neurol 2011; 70(11):960-969.

Chamberlain R, Reyes D, Curran G L, Marjanska M, Wengenack $T_M$, Poduslo J F, Garwood M, Jack C R. Comparison of amyloid plaque contrast generated by T2-weighted, T 2*-weighted, and susceptibility-weighted imaging methods in transgenic mouse models of Alzheimer's disease. Magnetic Resonance in Medicine 2009; 61(5):1158-1164.

Dickerson B C, Stoub T R, Shah R C, Sperling R A, Killiany R J, Albert M S, Hyman B T, Blacker D, Detoledo-Morrell L. Alzheimer-signature MRI biomarker predicts AD dementia in cognitively normal adults. Neurology 2011; 76(16):1395-1402.

Dickson J D, Ash T W, Williams G B, Sukstanskii A L, Ansorge R E, Yablonskiy D A. Quantitative phenomenological model of the BOLD contrast mechanism. J Magn Reson 2011; 212(1):17-25.

Fagan A M, Csernansky C A, Morris J C, Holtzman D M. The search for antecedent biomarkers of Alzheimer's disease. Journal of Alzheimer's disease: JAD 2005; 8(4): 347-358.

Fagan A M, Xiong C, Jasielec M S, Bateman R J, Goate A M, Benzinger T L, Ghetti B, Martins R N, Masters C L, Mayeux R, Ringman J M, Rossor M N, Salloway S, Schofield P R, Sperling R A, Marcus D, Cairns N J, Buckles V D, Ladenson J H, Morris J C, Holtzman D M, Dominantly Inherited Alzheimer N. Longitudinal change in CSF biomarkers in autosomal-dominant Alzheimer's disease. Sci Transl Med 2014; 6(226):226ra230.

Gomez-Isla T, Price J L, McKeel D W, Jr., Morris J C, Growdon R I, Hyman B T. Profound loss of layer II entorhinal cortex neurons occurs in very mild Alzheimer's disease. The Journal of neuroscience: the official journal of the Society for Neuroscience 1996; 16(14):4491-4500.

Hardy J, Allsop D. Amyloid deposition as the central event in the aetiology of Alzheimer's disease. Trends Pharmacol Sci 1991; 12(10):383-388.

Hardy J, Selkoe D J. The amyloid hypothesis of Alzheimer's disease: progress and problems on the road to therapeutics. Science 2002; 297(5580):353-356.

Hardy J A, Higgins G A. Alzheimer's disease: the amyloid cascade hypothesis. Science 1992; 256(5054):184-185.

He X, Yablonskiy D A. Quantitative BOLD: mapping of human cerebral deoxygenated blood volume and oxygen extraction fraction: default state. Magnetic Resonance in Medicine 2007; 57(1):115-126.

He X, Zhu M, Yablonskiy D A. Validation of oxygen extraction fraction measurement by qBOLD technique. Magn Reson Med 2008; 60(4):882-888.

Hoesen G W V. The human parahippocampal region in Alzheimer's disease, dementia, and ageing. In: Witter M P, Wouterlood F G, editors. The parahippocampal region: organization and role in cognitive function. Oxford; New York: Oxford University Press; 2002.

Hyman B T, Van Hoesen G W, Damasio A R, Barnes C L. Alzheimer's disease: cell-specific pathology isolates the hippocampal formation. Science 1984; 225(4667):1168-1170.

Ikonomovic M D, Klunk W E, Abrahamson E E, Mathis C A, Price J C, Tsopelas N D, Lopresti B J, Ziolko S, Bi W, Paljug W R, Debnath M L, Hope C E, Isanski B A, Hamilton R L, DeKosky S T. Post-mortem correlates of in vivo PiB-PET amyloid imaging in a typical case of Alzheimer's disease. Brain 2008; 131(Pt 6):1630-1645.

Jack C R, Jr., Knopman D S, Jagust W J, Shaw L M, Aisen P S, Weiner M W, Petersen R C, Trojanowski J Q. Hypothetical model of dynamic biomarkers of the Alzheimer's pathological cascade. The Lancet Neurology 2010; 9(1):119-128.

Jack C R, Jr., Petersen R C, Xu Y, O'Brien P C, Smith G E, Ivnik R J, Boeve B F, Tangalos E G, Kokmen E. Rates of hippocampal atrophy correlate with change in clinical status in aging and AD. Neurology 2000; 55(4):484-489.

Jenkinson M, Bannister P, Brady M, Smith S. Improved Optimization for the Robust and Accurate Linear Registration and Motion Correction of Brain Images. NeurolImage 2002; 17(2):825-841.

Jenkinson M, Beckmann C F, Behrens T E J, Woolrich M W, Smith S M. FSL. NeuroImage 2012; 62(2):782-790.

Juottonen K, Lehtovirta M, Helisalmi S, Riekkinen P J, Sr., Soininen H. Major decrease in the volume of the entorhinal cortex in patients with Alzheimer's disease carrying the apolipoprotein E epsilon4 allele. J Neurol Neurosurg Psychiatry 1998; 65(3):322-327.

Klunk W E, Engler H, Nordberg A, Wang Y, Blomqvist G, Holt D P, Bergstrom M, Savitcheva I, Huang G F, Estrada S, Ausen B, Debnath M T, Barletta J Price J C Sandell J Lopresti R J Wall A, Koivisto P, Antoni G, Mathis C A, Langstrom B. Imaging brain amyloid in Alzheimer's disease with Pittsburgh Compound-B. Annals of neurology 2004; 55(3):306-319.

Lee S-P, Falangola M F, Nixon R A, Duff K, Helpern J A. Visualization of β-amyloid plaques in a transgenic mouse model of Alzheimer's disease using MR microscopy without contrast reagents. Magnetic Resonance in Medicine 2004; 52(3):538-544.

Luo J, Jagadeesan B D, Cross A H, Yablonskiy D A. Gradient Echo Plural Contrast Imaging—Signal model and derived contrasts: T2*, Ti, Phase, SWI, T1f, FST2*and T2*-SWI. NeuroImage 2012; 60(2):1073-1082.

Luo J, Yablonskiy D A, Hildebolt C F, Lancia S, Cross A H. Gradient echo magnetic resonance imaging correlates with clinical measures and allows visualization of veins within multiple sclerosis lesions. Mult Scler 2014; 20(3):349-355.

Mamah D, Wen J, Luo J, Ulrich X, Barch D M, Yablonskiy D. Subcomponents of brain T2* relaxation in schizophrenia, bipolar disorder and siblings: A Gradient Echo Plural Contrast Imaging (GEPCI) study. Schizophr Res 2015.

McKhann G M, Knopman D S, Chertkow H, Hyman B T, Jack Jr C R, Kawas C H, Klunk W E, Koroshetz W J, Manly J J, Mayeux R, Mohs R C, Morris J C, Rossor M N, Scheltens P, Carrillo M C, Thies B, Weintraub S, Phelps C H. The diagnosis of dementia due to Alzheimer's disease: Recommendations from the National Institute on Aging-Alzheimer's Association workgroups on diagnostic guidelines for Alzheimer's disease. Alzheimer's & Dementia 2011; 7(3):263-269.

Meadowcroft M D, Connor J R, Smith M B, Yang Q X. MRI and histological analysis of beta-amyloid plaques in both human Alzheimer's disease and APP/PS1 transgenic mice. Journal of Magnetic Resonance Imaging 2009; 29(5):997-1007.

Mintun M A, Larossa G N, Sheline Y I, Dence C S, Lee S Y, Mach R H, Klunk W E, Mathis C A, DeKosky S T, Morris J C. [11C]PIB in a nondemented population: potential antecedent marker of Alzheimer disease. Neurology 2006; 67(3):446-452.

Mitchell T W, Mufson E J, Schneider J A, Cochran E J, Nissanov J, Han L Y, Bienias J L, Lee V M, Trojanowski J Q, Bennett D A, Arnold S E. Parahippocampal tau pathology in healthy aging, mild cognitive impairment, and early Alzheimer's disease. Annals of neurology 2002; 51(2):182-189.

Morris J C, Aisen P S, Bateman R J, Benzinger T L, Cairns N J, Fagan A M, Ghetti B, Goate A M, Holtzman D M, Klunk W E, McDade E, Marcus D S, Martins R N, Masters C L, Mayeux R, Oliver A, Quaid K, Ringman J M, Rossor M N, Salloway S, Schofield P R, Selsor N J, Sperling R A, Weiner M W, Xiong C, Moulder K L, Buckles V D. Developing an international network for Alzheimer research: The Dominantly Inherited Alzheimer Network. Clin Investig (Lond) 2012; 2(10):975-984.

Morris J C. The Clinical Dementia Rating (CDR): current version and scoring rules. Neurology 1993; 43(11):2412-2414.

Mugler J P, Brookeman J R. Three-dimensional magnetization-prepared rapid gradient-echo imaging (3D MP RAGE). Magnetic Resonance in Medicine 1990; 15(1):152-157.

Ogawa S, Lee $T_M$, Kay A R, Tank D W. Brain magnetic resonance imaging with contrast dependent on blood oxygenation. Proceedings of the National Academy of Sciences of the United States of America 1990; 87(24):9868-9872.

Patel K R, Luo J, Alvarez E, Piccio L, Schmidt R E, Yablonskiy D A, Cross A H. Detection of cortical lesions in multiple sclerosis: A new imaging approach. Multiple Sclerosis Journal—Experimental, Translational and Clinical 2015; 1.

Price J C, Klunk W E, Lopresti B J, Lu X, Hoge J A, Ziolko S K, Holt D P, Meltzer C C, DeKosky S T, Mathis C A. Kinetic modeling of amyloid binding in humans using PET imaging and Pittsburgh Compound-B. Journal of cerebral blood flow and metabolism: official journal of the International Society of Cerebral Blood Flow and Metabolism 2005; 25(11):1528-1547.

Price J L, Ko A I, Wade M J, Tsou S K, McKeel D W, Morris J C. Neuron number in the entorhinal cortex and CA1 in preclinical Alzheimer disease. Archives of neurology 2001; 58(9):1395-1402.

Price J L, Morris J C. Tangles and plaques in nondemented aging and "preclinical" Alzheimer's disease. Annals of neurology 1999; 45(3):358-368.

Quirk J D, Sukstanskii A L, Bretthorst G L, Yablonskiy D A. Optimal decay rate constant estimates from phased array data utilizing joint Bayesian analysis. J Magn Reson 2009; 198(1):49-56.

Reuter M, Schmansky N J, Rosas H D, Fischl B. Within-subject template estimation for unbiased longitudinal image analysis. NeuroImage 2012; 61(4):1402-1418.

Sati P, Cross A H, Luo J, Hildebolt C F, Yablonskiy D A. In vivo quantitative evaluation of brain tissue damage in multiple sclerosis using gradient echo plural contrast imaging technique. NeuroImage 2010; 51(3):1089-1097.

Scharfman H E, Witter M P, Schwarcz R. Preface. Annals of the New York Academy of Sciences 2000; 911(1):ix-xiii.

Schuff N, Woerner N, Boreta L, Kornfield T, Shaw L M, Trojanowski J Q, Thompson P M, Jack C R, Jr., Weiner M W, Alzheimer's Disease Neuroimaging I. MRI of hippocampal volume loss in early Alzheimer's disease in relation to ApoE genotype and biomarkers. Brain 2009; 132(Pt 4):1067-1077.

Selkoe D J. Alzheimer's disease. In the beginning. Nature 1991; 354(6353):432-433.

Spees W M, Yablonskiy D A, Oswood M C, Ackerman J J. Water proton MR properties of human blood at 1.5 Tesla: magnetic susceptibility, T(1), T(2), T*(2), and non-Lorentzian signal behavior. Magn Reson Med 2001; 45(4): 533-542.

Sperling R A, Aisen P S, Beckett L A, Bennett D A, Craft S, Fagan A M, Iwatsubo T, Jack C R, Jr., Kaye J, Montine T J, Park D C, Reiman E M, Rowe C C, Siemers E, Stern Y, Yaffe K, Carrillo M C, Thies B, Morrison-Bogorad M, Wagster M V, Phelps C H. Toward defining the preclinical stages of Alzheimer's disease: recommendations from the National Institute on Aging-Alzheimer's Association workgroups on diagnostic guidelines for Alzheimer's disease. Alzheimer's & dementia: the journal of the Alzheimer's Association 2011; 7(3):280-292.

Su Y, D'Angelo G M, Vlassenko A G, Zhou G, Snyder A Z, Marcus D S, Blazey $T_M$, Christensen J J, Vora S, Morris J C, Mintun M A, Benzinger T L. Quantitative analysis of PiB-PET with FreeSurfer ROIs. PloS one 2013; 8(11): e73377.

Thangavel R, Van Hoesen G W, Zaheer A. Posterior parahippocampal gyrus pathology in Alzheimer's disease. Neuroscience 2008; 154(2):667-676.

Ulrich X, Yablonskiy D A. Separation of cellular and BOLD contributions to T2* signal relaxation. Magn Reson Med 2015; DOI: 10.1002/mrm.25610.

Wang X, Sukstanskii A L, Yablonskiy D A. Optimization strategies for evaluation of brain hemodynamic parameters with qBOLD technique. Magn Reson Med 2013; 69(4):1034-1043.

Wen J, Cross A H, Yablonskiy D A. On the role of physiological fluctuations in quantitative gradient echo MRI: implications for GEPCI, QSM, and SWI. Magnetic resonance in medicine: official journal of the Society of Magnetic Resonance in Medicine/Society of Magnetic Resonance in Medicine 2014.

Wen J, Yablonskiy D A, Luo J, Lancia S, Hildebolt C, Cross A H. Detection and quantification of regional cortical gray matter damage in multiple sclerosis utilizing gradient echo MRI. NeuroImage: Clinical 2015; 9:164-175.

Wengenack $T_M$, Reyes D A, Curran G L, Borowski B J, Lin J, Preboske G M, Holasek S S, Gilles E J, Chamberlain R, Marjanska M, Jack C R, Jr., Garwood M, Poduslo J F. Regional differences in MRI detection of amyloid plaques in AD transgenic mouse brain. NeuroImage 2011; 54(1): 113-122.

Yablonskiy D A, Haacke E M. Theory of NMR signal behavior in magnetically inhomogeneous tissues: the static dephasing regime. Magn Reson Med 1994; 32(6): 749-763.

Yablonskiy D A, Luo J, Sukstanskii A L, Iyer A, Cross A H. Biophysical mechanisms of MRI signal frequency contrast in multiple sclerosis. Proc Natl Acad Sci USA 2012; 109(35):14212-14217.

Yablonskiy D A, Sukstanskii A L, He X. Blood oxygenation level-dependent (BOLD)-based techniques for the quantification of brain hemodynamic and metabolic properties—theoretical models and experimental approaches. NMR in biomedicine 2013; 26(8):963-986.

Yablonskiy D A, Sukstanskii A L, Luo J, Wang X. Voxel spread function method for correction of magnetic field inhomogeneity effects in quantitative gradient-echo-based MRI. Magn Reson Med 2013; 70(5):1283-1292.

Yablonskiy D A. Gradient echo plural contrast imaging (GEPCI)—New fast magnetic resonance imaging technique for simultaneous acquisition of T2, T1 (or spin density) and T2*-weighted images. RSNA Annual Meeting. Volume 217S. Chicago, Ill.; 2000. p 204.

Yablonskiy D A. Quantitation of intrinsic magnetic susceptibility-related effects in a tissue matrix. Phantom study. Magnetic Resonance in Medicine 1998; 39(3):417-428.

Yablonskiy D A. Quntitative T2 contrast with Gradient Echoes. 8th Annual Meeting of the International Society for Magnetic Resonance in Medicine. Denver, Colo.; 2000.

Zhao Y, Wen J, Cross A H, Yablonskiy D A. On the relationship between cellular and hemodynamic properties of the human brain cortex throughout adult lifespan. NeuroImage 2016.

Zhao Y, Wen J, Cross A H, Yablonskiy D A. On the Relationship Between Cellular and Hemodynamic Properties of the Human Brain Cortex Throughout Adult Lifespan. 2015; 10th Biennial Minnesota High Field Workshop.

What is claimed is:

1. A method of measuring β-amyloid in a subject comprising:
   obtaining magnetic resonance imaging (MRI) data from the brain of a subject using a gradient echo magnetic resonance imaging (MRI) technique; and
   extracting R2* values from the MRI data,
   wherein
   an increase in R2* in a brain region compared to the R2* of a normal control indicates that the subject has increased accumulation of β-amyloid.

2. The method of claim 1, wherein the gradient echo MRI technique is a gradient echo plural contrast imaging (GEPCI) MRI technique.

3. The method of claim 1 or 2, wherein the brain region is selected form the group consisting of: the precuneus, fusiform, lingual, paracentral, rostral-anterior cingulate, parahippocampus, and combinations thereof.

4. The method of claim 1, further comprising using a voxel spread function method to account for the adverse effects of field inhomogeneities.

5. The method of claim 1, further comprising using navigator echoes to account for the adverse effects of physiological fluctuations.

6. The method of claim 1, further comprising mapping oxygen extraction fraction, deoxygenated cerebral blood volume, and the concentration of tissue deoxyhemoglobin.

7. The method of claim 1, further comprising extracting R2t* values from the MRI data.

8. The method of claim 7, wherein R2* and R2t* are measured simultaneously.

9. The method of claim 7, wherein increased R2* and decreased R2t* indicate accumulation of β-amyloid and tau, correspondingly.

10. The method of claim 1, if the subject is a cognitively normal (CDR=0)-subject and has increased R2* values, the AD is preclinical AD.

11. A method of measuring loss of cellular integrity in the brain of a subject comprising:
   obtaining magnetic resonance imaging (MRI) data from the brain of a subject using a gradient echo magnetic resonance imaging (MRI) technique; and
   extracting values of R2t*-a tissue specific component of R2* from the MRI data in a brain regions;

wherein a decrease in R2t* in the brain region indicates that the subject has loss of cellular integrity in the brain region.

12. The method of claim 11, wherein the gradient echo MRI technique is a gradient echo plural contrast imaging (GEPCI) MRI technique.

13. The method of claim 11, wherein the brain region consists of the hippocampus.

14. The method of claim 11, further comprising extracting R2* from the MRI data.

15. The method of claim 14, wherein R2* and R2t* are measured simultaneously.

16. The method of claim 14, wherein increased R2* and decreased R2t* indicate accumulation of β-amyloid and tau, correspondingly.

17. A method of diagnosing Alzheimer's Disease (AD) in a subject comprising:
obtaining magnetic resonance imaging (MRI) data from the brain of a subject using gradient echo magnetic resonance imaging (MRI) technique; and
extracting values of R2t*-a tissue-specific component of R2* in a brain region,
wherein
a decrease in R2t* values in the brain region compared to a normal control indicates that the subject has AD.

18. The method of claim 17, further comprising measuring R2* values in a brain region, wherein
an increase in R2* values in the R2*-specific brain regions relative to a normal control and equivalent R2t* in the R2t*-specific brain regions relative to a normal control, indicate that the subject has pre-clinical AD; or
an increase in R2* values in the R2*-specific brain regions relative to a normal control and a decrease in R2t* values in the R2t*-specific brain region relative to a normal control indicates that the subject has clinical AD.

19. The method of claim 18, wherein a decrease in R2t* in the R2t*-specific brain region and increase in R2* in the R2*-specific brain region relative to a normal control indicates that the subject has accumulation of tau proteins and β-amyloid in the brain region.

20. A system for measuring amyloid concentration in the brain comprising:
an MRI device,
a first processor for determining the ΔR2* and the phenomenological relationship between ΔR2* and β-amyloid concentration;
a second processor for determining the ΔR2t* in a region of the brain and the phenomenological relationship between ΔR2t* and loss of tissue cellular density or cellular integrity; and
a display.

21. The system of claim 20, wherein the processor further accounts for the contribution of magnetic field inhomogeneities on transverse relaxation, artifacts related to physiological fluctuations, oxygen extraction fraction, deoxygenated cerebral blood volume, and/or the concentration of tissue deoxyhemoglobin.

22. The system of claim 20, wherein the first processor for determining the ΔR2t* and the second processor for determining ΔR2* are the same processor.

23. A system for diagnosing Alzheimer's disease comprising:
an MRI device;
a processor for determining a combination of GEPCI surrogate markers of β-amyloid burden, ΔR2*, and tissue cellular loss or cellular integrity, ΔR2t*; and
a processor for distinguishing between normal, preclinical, and mild AD groups; and a display.

24. The system for diagnosing Alzheimer's disease of claim 23, wherein the processor for determining the combination of GEPCI surrogate markers and the processor for distinguishing between normal, preclinical, and mild AD groups is the same processor.

25. A method of detecting R2*, a biomarker for AD, comprising:
obtaining magnetic resonance imaging (MRI) data from the parahippocampal region of the brain of a subject; and
extracting an R2* value from the MRI data,
wherein
R2* is a surrogate measurement of accumulation of β-amyloid; and
the MRI data is generated from a gradient echo MRI sequence.

26. A method of detecting R2t*, a biomarker for AD, comprising:
obtaining magnetic resonance imaging (MRI) data from the hippocampal region of the brain of the subject; and
extracting a R2t* value from the MRI data, wherein
R2t* is a surrogate measurement of changes in tissue cellular density or tissue cellular integrity; and
the MRI data is generated from a gradient echo MRI pulse sequence.

27. A method of detecting a change in severity of AD, comprising
obtaining a first set magnetic resonance imaging (MRI) data of the brain of a subject at an earlier time; and
obtaining a second set magnetic resonance imaging (MRI) data of the brain of a subject at a later time;
wherein
an increase in R2* values and a decrease in R2t* values extracted from the second set of MRI data compared to the R2* and R2t* values extracted from the first set of MRI data, indicates that the subject has an increase in severity of AD.

28. A system for measuring loss of tissue cellular density or cellular integrity in the brain comprising:
an MRI device;
a processor for determining the ΔR2t* in a regions of the brain and the phenomenological relationship between ΔR2t* and loss of tissue cellular density or cellular integrity; and
a display.

29. A system for diagnosing Alzheimer's disease comprising an MRI device; a processor for determining the ΔR2* and ΔR2t* in regions of the brain, a phenomenological relationship between ΔR2* and ΔR2t* in regions of the brain, and severity of Alzheimer's disease; and a display.

* * * * *